US009437093B2

(12) United States Patent
Julicher et al.

(10) Patent No.: US 9,437,093 B2
(45) Date of Patent: Sep. 6, 2016

(54) DIFFERENTIAL CURRENT MEASUREMENTS TO DETERMINE ION CURRENT IN THE PRESENCE OF LEAKAGE CURRENT

(71) Applicant: Microchip Technology Incorporated, Chandler, AZ (US)

(72) Inventors: Joseph Julicher, Maricopa, AZ (US); Keith Curtis, Gilbert, AZ (US); Paul N. Katz, Bellaire, TX (US)

(73) Assignee: MICROCHIP TECHNOLOGY INCORPORATED, Chandler, AZ (US)

( * ) Notice: Subject to any disclaimer, the term of this patent is extended or adjusted under 35 U.S.C. 154(b) by 486 days.

(21) Appl. No.: 13/633,686

(22) Filed: Oct. 2, 2012

(65) Prior Publication Data

US 2013/0088238 A1    Apr. 11, 2013

Related U.S. Application Data

(60) Provisional application No. 61/570,485, filed on Dec. 14, 2011, provisional application No. 61/570,418, filed on Dec. 14, 2011, provisional application No. 61/570,436, filed on Dec. 14, 2011, provisional (Continued)

(51) Int. Cl.
*G01N 27/66* (2006.01)
*G08B 17/11* (2006.01)

(52) U.S. Cl.
CPC .............. *G08B 17/11* (2013.01); *G01N 27/66* (2013.01)

(58) Field of Classification Search
USPC ....................................................... 324/469
See application file for complete search history.

(56) References Cited

U.S. PATENT DOCUMENTS 3,295,121 A    12/1966   Scheel ........................ 340/629
3,832,678 A     8/1974   Gysell et al. ................ 340/587

(Continued)

FOREIGN PATENT DOCUMENTS

CN         1087739 A     6/1994    ............. G08B 17/11
CN       101261225 A     9/2008    ............. G01N 21/53

(Continued)

OTHER PUBLICATIONS

Yair, R., "Charge Sampling Method for Low Current Measurement," Review of Scientific Instruments, vol. 45, No. 3, 6 pages, Mar. 1974.

(Continued)

*Primary Examiner* — Melissa Koval
*Assistant Examiner* — Courtney McDonnough
(74) *Attorney, Agent, or Firm* — Slayden Grubert Beard PLLC

(57) ABSTRACT

An ion chamber provides a current representative of its characteristics as affected by external conditions, e.g., clean air or smoke. A direct current (DC) voltage is applied to the ion chamber at a first polarity and the resulting current through the ion chamber and parasitic leakage current is measured at the first polarity, then the DC voltage is applied to the ion chamber at a second polarity opposite the first polarity, and the resulting current through the ion chamber and parasitic leakage current is measured at the second polarity. Since substantially no current flows through the ion chamber at the second polarity, the common mode parasitic leakage current contribution may be removed from the total current measurement by subtracting the current measured at the second polarity from the current measured at the first polarity, resulting in just the current through the ion chamber.

31 Claims, 18 Drawing Sheets

Related U.S. Application Data application No. 61/578,502, filed on Dec. 21, 2011, provisional application No. 61/544,386, filed on Oct. 7, 2011, provisional application No. 61/544,150, filed on Oct. 6, 2011, provisional application No. 61/544,363, filed on Oct. 7, 2011.

(56) References Cited

U.S. PATENT DOCUMENTS

| | | | |
|---|---|---|---|
| 4,213,047 A | 7/1980 | Mccord | 250/381 |
| 4,222,045 A | 9/1980 | Cholin | 340/628 |
| 4,260,984 A | 4/1981 | Honma | 340/630 |
| 4,266,220 A | 5/1981 | Malinowski | 340/360 |
| 4,401,978 A | 8/1983 | Solomon | 340/628 |
| 4,538,137 A | 8/1985 | Kimura | 340/512 |
| 4,652,866 A | 3/1987 | Siegmann et al. | 340/628 |
| 5,173,683 A | 12/1992 | Brighenti et al. | 340/505 |
| 5,243,330 A | 9/1993 | Thuillard | 340/629 |
| 5,422,807 A | 6/1995 | Mitra et al. | 700/79 |
| 5,705,988 A | 1/1998 | Mcmaster | 340/628 |
| 5,966,078 A | 10/1999 | Tanguay | 340/636.1 |
| 6,257,049 B1 | 7/2001 | Greybush | 73/29.01 |
| 6,433,712 B1 | 8/2002 | Ohnhaeuser et al. | 341/141 |
| 6,661,346 B1 | 12/2003 | Wood et al. | 340/601 |
| 6,981,090 B1 | 12/2005 | Kutz et al. | 710/317 |
| 7,288,946 B2 | 10/2007 | Hargreaves et al. | 324/678 |
| 7,307,485 B1 | 12/2007 | Snyder et al. | 331/150 |
| 7,382,140 B2 | 6/2008 | Obrecht | 324/678 |
| 7,460,441 B2 | 12/2008 | Bartling | 368/118 |
| 7,764,213 B2 | 7/2010 | Bartling et al. | 341/152 |
| 7,834,773 B2 | 11/2010 | Kato | 340/630 |
| 8,847,802 B2 | 9/2014 | Lundstrum et al. | 341/141 |
| 8,884,771 B2 | 11/2014 | Cooke et al. | 340/628 |
| 9,035,243 B2 | 5/2015 | Lenkeit et al. | 250/287 |
| 2002/0078744 A1 | 6/2002 | Gehman et al. | 73/204.11 |
| 2002/0101345 A1 | 8/2002 | Pattok et al. | 340/516 |
| 2002/0153923 A1 | 10/2002 | Piasecki et al. | 326/57 |
| 2003/0058114 A1 | 3/2003 | Miller | 340/577 |
| 2004/0257235 A1 | 12/2004 | Right et al. | 340/628 |
| 2005/0030172 A1 | 2/2005 | Right et al. | 340/521 |
| 2007/0075710 A1 | 4/2007 | Hargreaves et al. | 324/658 |
| 2008/0012715 A1 | 1/2008 | Montgomery | 340/579 |
| 2008/0272826 A1 | 11/2008 | Smit et al. | 327/509 |
| 2008/0312857 A1 | 12/2008 | Sequine | 702/65 |
| 2009/0230305 A1 | 9/2009 | Burke et al. | 250/336.1 |
| 2010/0102832 A1 | 4/2010 | Bartling et al. | 324/679 |
| 2010/0181180 A1 | 7/2010 | Peter | 200/5 R |
| 2010/0231241 A1 | 9/2010 | Mueck et al. | 324/686 |
| 2010/0283760 A1 | 11/2010 | Leung et al. | 345/174 |
| 2010/0295555 A1 | 11/2010 | Emanuel et al. | 324/601 |
| 2011/0007028 A1 | 1/2011 | Curtis et al. | 345/174 |
| 2011/0267287 A1 | 11/2011 | Bartling et al. | 345/173 |
| 2011/0267309 A1 | 11/2011 | Hanauer et al. | 345/174 |
| 2013/0126715 A1 | 5/2013 | Flaherty | 250/214 R |

FOREIGN PATENT DOCUMENTS

| | | | | |
|---|---|---|---|---|
| CN | 102257543 A | 11/2011 | | G08B 11/00 |
| DE | 10357371 A1 | 7/2005 | | G08B 17/00 |
| DE | 102009030495 A1 | 1/2011 | | G01B 7/00 |
| EP | 1719947 A1 | 11/2006 | | F23N 5/12 |
| FR | 2473201 A1 | 7/1981 | | G08B 17/11 |
| GB | 1598821 A | 9/1981 | | G08B 17/11 |
| GB | 2117560 A | 10/1983 | | G01N 27/64 |
| GB | 2156126 A | 10/1985 | | G08B 17/00 |
| WO | 2006/138205 A1 | 12/2006 | | H03M 1/06 |

OTHER PUBLICATIONS

Margarita, Andrey, "Application Note AN2245: Smart Smoke Detector," Cypress Semiconductor Corporation, XP055054690, URL: http://www.psocdeveloper.com/uploads/tx_piapappnote/an2245_01.pdf, 12 pages, Feb. 22, 2005.

Perme, Thomas, "AN1101: Introduction to Capacitive Sensing," Microchip Technology, Inc., XP002693941, URL: http://ww1.microchip.com/downloads/en/AppNotes/01101A.pdf, 10 pages, Jun. 25, 2007.

Bohn, Bruce, "AN1250: Microchip CTMU for Capacitive Touch Applications," Microchip Technology, Inc., XP055007432, URL: http://www.microchip.com/stellent/ideplg?IdcService=SS_GET_PAGE&nodeID=1824&appnote=en539441, 22 pages, Feb. 3, 2009.

Perme, Thomas et al., AN1298: Capacitive Touch Using Only an ADC ("CVD"), Microchip Technology, Inc., XP055007357, URL: http://www.microchip.com/stellent/ideplg?IdcService=SS_GET_PAGE&nodeId=1824&appnote=en545264, 4 pages, Oct. 7, 2009.

Davison, Burke, "AN1334: Techniques for Robust Touch Sensing Design," Microchip Technology, Inc., XP055047201, URL: http://www.microchip.com/downloads/en/AppNotes/01334A.pdf, 28 pages, Aug. 6, 2010.

Yedamale, Padmaraja et al., "AN1375: See What You Can Do with the CTMU," Microchip Technology, Inc., XP055047211, URL: http://www.microchip.com/downloads/en/AppNotes/CTMU%2001375a.pdf, 12 pages, May 11, 2011.

Anonymous, "Delta-Sigma Modulation," Wikipedia, URL: http://en.wikipedia.org/w/index.php?title=Special:Book&bookcmd=download&collection_id=fa136df1282a073a&writer=r1&return_to=Delta-sigma modulation, 14 pages, 2012.

International Search Report and Written Opinion, Application No. PCT/US2012/058682, 12 pages, Dec. 17, 2012.

International Search Report and Written Opinion, Application No. PCT/US2012/058691, 13 pages, Dec. 19, 2012.

International Search Report and Written Opinion, Application No. PCT/US2012/058832, 11 pages, Jan. 22, 2013.

International Search Report and Written Opinion, Application No. PCT/US2012/058837, 14 pages, Feb. 18, 2013.

International Search Report and Written Opinion, Application No. PCT/US2012/058716, 10 pages, Mar. 15, 2013.

International Search Report and Written Opinion, Application No. PCT/US2012/069086, 10 pages, Apr. 5, 2013.

International Search Report and Written Opinion, Application No. PCT/US2012/069094, 12 pages, Apr. 5, 2013.

International Search Report and Written Opinion, Application No. PCT/US2012/058688, 11 pages, Apr. 5, 2013.

International Search Report and Written Opinion, Application No. PCT/US2012/069076, 11 pages, Apr. 10, 2013.

International Search Report and Written Opinion, Application No. PCT/US2012/070466, 13 pages, Apr. 24, 2013.

International Search Report and Written Opinion, Application No. PCT/US2013/052956, 12 pages, Jan. 28, 2014.

U.S. Advisory Action, U.S. Appl. No. 13/709,399, 3 pages, Sep. 8, 2015.

Cuilan, Tan, Research & Design of Wireless Smoke Detection System, Engineering Science and technology II, China Master's Theses (Chinese language), 1 page (English abstract), Sep. 15, 2009.

Chinese Office Action, Application No. 201280068100.7, 5 pages, Oct. 9, 2015.

DIFFERENTIAL CURRENT MEASUREMENTS TO DETERMINE ION CURRENT IN THE PRESENCE OF LEAKAGE CURRENT

RELATED PATENT APPLICATIONS

This application claims priority to commonly owned U.S. Provisional Patent Application Ser. No. 61/570,485; filed Dec. 14, 2011; entitled "Method and Apparatus for Detecting Smoke," by Benjamin T. Cooke, Joseph Julicher and Keith Edwin Curtis; U.S. Provisional Patent Application Ser. No. 61/570,418; filed Dec. 14, 2011; entitled "Method and Apparatus for Detecting Smoke," by Benjamin T. Cooke, Joseph Julicher and Keith Edwin Curtis; U.S. Provisional Patent Application Ser. No. 61/570,436; filed Dec. 14, 2011; entitled "Method and Apparatus for Detecting Smoke," by Benjamin T. Cooke, Joseph Julicher and Keith Edwin Curtis; U.S. Provisional Patent Application Ser. No. 61/578,502; filed Dec. 21, 2011; entitled "Current/Voltage Interface," by Joseph Julicher; U.S. Provisional Patent Application Ser. No. 61/544,386; filed Oct. 7, 2011; entitled "ADC With Internal Charge/Discharge Switches," by Zeke Lundstrum, Keith Curtis, Burke Davison, Sean Steedman and Yann LeFaou; U.S. Provisional Patent Application Ser. No. 61/544,150; filed Oct. 6, 2011; entitled "Microcontroller ADC with Guard Ring Drive Outputs," by Zeke Lundstrum, Keith Curtis, Burke Davison, Sean Steedman and Yann LeFaou; and U.S. Provisional Patent Application Ser. No. 61/544,363; filed Oct. 7, 2011; entitled "Microcontroller ADC with External Access to the Analog Input Bus," by Zeke Lundstrum, Keith Curtis, Burke Davison, Sean Steedman and Yann LeFaou; wherein all of which are hereby incorporated by reference herein for all purposes.

TECHNICAL FIELD

The present disclosure relates to an ion chamber interface, and, in particular, for a microcontroller having a current input interface that rejects common mode current leakage in determining ion current in the presence of the leakage current.

BACKGROUND

A smoke detector generally uses an ionization chamber containing a radioactive ion source that is coupled to a high input impedance operational amplifier. A typical ionization chamber, used in a smoke detector, provides a very small current (nA) that is reduced in the presence of smoke particles. Operational amplifiers are used to convert this current to a voltage that is then measured to determine the presence of smoke. Elevated temperatures cause increased leakage currents on the inputs of the operational amplifier in the smoke detector. This affects overall performance of the ionization chamber smoke detection function. Thus, such increases in leakage currents can pose a variety of problems such as inaccuracy, etc. which may require further compensation circuits when designing a smoke detector and therefore may increase the cost of the device.

Furthermore, the impedance of the ion chamber is extremely high, and any leakage currents, e.g., printed circuit board leakage current, masks the ion chamber current. Smoke detection ion chambers therefore require a complex manufacturing process where pins of the sensing integrated circuit operational amplifier are bent and directly welded in mid-air to the ion chamber. As mentioned above, special low leakage circuits are required to detect the small current change through the ion chamber caused by the presence of smoke therein.

SUMMARY

Therefore, a need exists for a way to detect smoke in an ion chamber of a smoke detector that does not require sensitive and expensive components nor complex manufacturing processes.

According to an embodiment, a method for determining ion current in an ion chamber may comprise the steps of: coupling first and second electrodes of an ion chamber to a voltage at a first polarity; determining a first current between the first and the second electrodes of the ion chamber caused by the voltage at the first polarity; coupling the first and the second electrodes of the ion chamber to the voltage at a second polarity; determining a second current between the first and the second electrodes of the ion chamber caused by the voltage at the second polarity; and determining a difference between the first and second currents, wherein the difference may be the ion current through the ion chamber.

According to a further embodiment of the method, the second polarity may be opposite the first polarity. According to a further embodiment of the method, the voltage may be a direct current (DC) voltage. According to a further embodiment of the method, the ion chamber may comprise a radiation source for ionizing gas molecules therein. According to a further embodiment of the method, the ion chamber may be used to detect smoke particles.

According to a further embodiment of the method, the step of determining the difference between the first and second currents may comprise the steps of: storing the first and second current measurements in a memory; and subtracting one current measurement from the other current measurement. According to a further embodiment of the method, the voltage may be a plurality of voltage pulses.

According to another embodiment, a method for determining ion current in an ion chamber may comprise the steps of: setting a capacitor to a starting voltage; coupling a first electrode of an ion chamber to a supply voltage; coupling a second electrode of the ion chamber to the capacitor; charging the capacitor for a first period of time; converting a first charge voltage on the capacitor to a first digital representation thereof; storing the first digital representation in a memory; setting the capacitor to the starting voltage; coupling the second electrode of the ion chamber to the supply voltage; coupling the first electrode of the ion chamber to the capacitor; charging the capacitor for a second period of time; converting a second charge voltage on the capacitor to a second digital representation thereof; storing the second digital representation in the memory; and determining a difference between the first and second digital representations, wherein the difference may be a digital representation of the ion current in the ion chamber.

According to a further embodiment of the method, the starting voltage may be substantially zero (0) volts. According to a further embodiment of the method, the starting voltage may be substantially the supply voltage. According to a further embodiment of the method, may comprise the step of determining whether the difference may be in an alarm condition range. According to a further embodiment of the method, may comprise the step of actuating an alarm when the difference may be in the alarm condition range. According to a further embodiment of the method, the voltage may be a pulse generator comprising a plurality of output voltage pulses. According to a further embodiment of the method, may comprise the step of charging a guard ring around the ion chamber to a voltage on the capacitor.

According to yet another embodiment, a method for determining ion current in an ion chamber may comprise the steps of: setting a capacitor to a starting voltage; coupling a first electrode of an ion chamber to a pulse source; coupling a second electrode of the ion chamber to the capacitor; charging the capacitor with a plurality of pulses from the pulse source for a first period of time; counting a first number of the plurality of pulses required to charge the capacitor to a second voltage; storing the first number in a memory; setting the capacitor to the supply voltage; coupling the second electrode of the ion chamber to the pulse source; coupling the first electrode of the ion chamber to the capacitor; charging the capacitor with the plurality of pulses from the pulse source for a second period of time; counting a second number of the plurality of pulses required to charge the capacitor to the second voltage; storing the second number in a memory; and determining a difference between the first and second numbers, wherein the difference may be a digital representation of the ion current in the ion chamber.

According to a further embodiment of the method, the starting voltage may be substantially zero (0) volts. According to a further embodiment of the method, the starting voltage may be substantially the supply voltage. According to a further embodiment of the method, may comprise the step of determining whether the difference may be in an alarm condition range. According to a further embodiment of the method, may comprise the step of actuating an alarm when the difference may be in the alarm condition range. According to a further embodiment of the method, the step of charging a guard ring around the ion chamber to a voltage on the capacitor.

According to still another embodiment, a method for determining ion current in an ion chamber may comprise the steps of: setting a capacitor to a first voltage; coupling a first electrode of an ion chamber to a plurality of voltage transitions having time periods and voltage amplitudes from substantially zero volts to substantially a voltage; coupling a second electrode of the ion chamber to the capacitor; charging and discharging the capacitor with the plurality of voltage transitions having the defined time periods; and counting a number of transitions of the plurality of voltage transitions required to charge the capacitor to a second voltage.

According to a further embodiment of the method, may comprise the step of determining whether the number of transitions represents an alarm condition range.

According to a further embodiment of the method, may comprise the steps of: measuring a charge voltage on the capacitor; and adjusting the time periods for the plurality of voltage transitions when at substantially zero volts and at substantially the voltage, wherein: when the charge voltage on the capacitor may be less than one-half the voltage, the time periods of the plurality of voltage transitions when at the zero volt amplitude may be greater than the time periods of the plurality of voltage transitions when at the voltage amplitude; when the charge voltage on the capacitor may be at substantially one-half the voltage, the time periods of the zero volt and voltage amplitudes of the plurality of voltage transitions may be substantially the same; and when the charge voltage on the capacitor may be greater than one-half the voltage, the time periods of the plurality of voltage transitions when at the zero volt amplitude may be less than the time periods of the plurality of voltage transitions when at the voltage amplitude.

According to a further embodiment of the method, may comprise the step of charging a guard ring around the ion chamber to substantially the charge voltage on the capacitor.

According to another embodiment, a method for determining ion current in an ion chamber may comprise the steps of: setting a capacitor to a starting voltage; coupling an ion chamber and a capacitor in series to a supply voltage at a first polarity; charging the capacitor for a first time period; coupling the ion chamber and the capacitor in series to the supply voltage at a second polarity; discharging the capacitor for a second time period; and measuring a charge voltage on the capacitor after a detection time period.

According to a further embodiment of the method, the starting voltage may be substantially zero (0) volts. According to a further embodiment of the method, the starting voltage may be substantially the supply voltage. According to a further embodiment of the method, may comprise the step of determining whether the measured charge voltage may be in an alarm condition range. According to a further embodiment of the method, may comprise the step of actuating an alarm when the measured charge voltage may be in the alarm condition range. According to a further embodiment of the method, the supply voltage may be a pulse generator having an output comprising a plurality of voltage pulses. According to a further embodiment of the method, may comprise the step of charging a guard ring around the ion chamber to substantially the charge voltage on the capacitor.

According to another embodiment, an apparatus for detecting smoke may comprise: an ionization chamber having a radiation source and comprising first and second electrodes, wherein the ionization chamber may be open to smoke ingress; and a microcontroller comprising: a first switch coupled to the first electrode of the ionization chamber; a second switch coupled to the second electrode of the ionization chamber; a digital driver having an output coupled to first positions of the first and second switches; a capacitor coupled to second positions of the first and second switches; a third switch coupled between the capacitor and a power supply common, the third switch adapted for discharging the capacitor; a timer coupled to an input of the digital driver, wherein the timer generates a pulse having a time period; an analog-to-digital converter (ADC); a fourth switch coupled between the capacitor and the ADC; and a digital processor and memory, wherein the digital processor may be coupled to and controls the first, second, third and fourth switches; and the ADC and timer may be coupled to the digital processor; wherein when the first switch may be in the first position the first electrode of the ionization chamber may be coupled to the digital driver, when the first switch may be in the second position the first electrode of the ionization chamber may be coupled to the capacitor, when the second switch may be in the first position the second electrode of the ionization chamber may be coupled to the digital driver, when the second switch may be in the second position the second electrode of the ionization chamber may be coupled to the capacitor; when the third switch may be closed the capacitor may be at substantially zero (0) volts; and when the fourth switch may be closed the capacitor may be coupled to the ADC.

According to a further embodiment, the ionization chamber may comprise: two chambers separated by a third electrode, wherein one of the two chambers may be open to smoke ingress and the other may be closed to smoke ingress; a fifth switch coupled to the third electrode; the first and fifth switches have three positions wherein the third position may be open; the digital driver may be coupled to a first position of the fifth switch; and the capacitor may be coupled to a second position of the fifth switch.

According to a further embodiment, the microcontroller may comprise an alarm driver. According to a further embodiment, an audible/visual alarm may be coupled to the alarm driver. According to a further embodiment, a guard ring may be around the ion chamber, wherein the guard ring may be charged to a guard ring voltage substantially the same as a charge voltage on the capacitor. According to a further embodiment, a second capacitor may be coupled to the capacitor.

According to another embodiment, an apparatus for detecting smoke may comprise: an ionization chamber having a radiation source and comprising first and second electrodes, wherein the ionization chamber may be open to smoke ingress; and an integrated circuit comprising: a first switch coupled to the first electrode of the ionization chamber; a second switch coupled to the second electrode of the ionization chamber; a digital driver having an output coupled to first positions of the first and second switches; a voltage comparator having a first input coupled to second positions of the first and second switches and a second input coupled to a voltage reference; a capacitor coupled between the first and second inputs of the voltage comparator; a flip-flop having a D-input coupled to an output of the voltage comparator and a clock input coupled to a clock generator, wherein each time a clock signal may be received from the clock generator a logic value at the D-input may be transferred to a Q-output of the flip-flop; a feedback resistor coupled between the Q-output of the flip-flop and the first input of the voltage comparator for charging and discharging the capacitor; a current measurement resistor coupled between the first input of the voltage comparator and a power supply common; wherein when a voltage on the first input of the voltage comparator may be greater than a voltage from the voltage reference the output of the voltage comparator may be at a logic low and the capacitor may be discharged, and when the voltage on the first input of the voltage comparator may be less than the voltage from the voltage reference the output of the voltage comparator may be at a logic high and the capacitor may be charged; a first counter for counting a first number of clock pulses from the clock generator when the Q-output of the flip-flop may be at a logic high during a certain time period; and a second counter for counting a second number of clock pulses from the clock generator during a certain time period; wherein when the first switch may be in the first position the first electrode of the ionization chamber may be coupled to the digital driver, when the first switch may be in the second position the first electrode of the ionization chamber may be coupled to the first input of the voltage comparator, when the second switch may be in the first position the second electrode of the ionization chamber may be coupled to the digital driver, and when the second switch may be in the second position the second electrode of the ionization chamber may be coupled to the first input of the voltage comparator.

According to a further embodiment, the integrated circuit may be a microcontroller having a digital processor and memory. According to a further embodiment, the digital processor and memory of the microcontroller may go into a low power sleep mode during counting by the first and second counters. According to a further embodiment, the integrated circuit may comprise an alarm driver. According to a further embodiment, an audible/visual alarm may be coupled to the alarm driver. According to a further embodiment, a guard ring may be around the ion chamber, wherein the guard ring may be charged to a guard ring voltage substantially the same as a charge voltage on the capacitor. According to a further embodiment, a second capacitor may be coupled to the capacitor.

According to another embodiment, an apparatus for detecting smoke may comprise: an ionization chamber having a radiation source and comprising first and second electrodes, wherein the ionization chamber may be open to smoke ingress; and a microcontroller may comprise: a first switch coupled to the first electrode of the ionization chamber; a second switch coupled to the second electrode of the ionization chamber; a digital driver having an output coupled to first positions of the first and second switches; a capacitor coupled to second positions of the first and second switches; a third switch coupled between the capacitor and a power supply common, the third switch adapted for discharging the capacitor; a voltage comparator having a first input coupled to the capacitor and a second input coupled to a voltage reference; a pulse generator coupled to an input of the digital driver; a pulse counter coupled to the pulse generator, wherein the pulse counter counts an number of pulses from the pulse generator; and a digital processor and memory, wherein the digital processor may be coupled to and controls the first, second and third switches, the pulse generator and the counter pulse; wherein when the first switch may be in the first position the first electrode of the ionization chamber may be coupled to the digital driver, when the first switch may be in the second position the first electrode of the ionization chamber may be coupled to the capacitor, when the second switch may be in the first position the second electrode of the ionization chamber may be coupled to the digital driver, when the second switch may be in the second position the second electrode of the ionization chamber may be coupled to the capacitor; and when the third switch may be closed the capacitor may be at substantially zero (0) volts.

According to a further embodiment, the digital processor and memory of the microcontroller may go into a low power sleep mode during pulse counting by the pulse counter. According to a further embodiment, the microcontroller further may comprise an alarm driver. According to a further embodiment, an audible/visual alarm may be coupled to the alarm driver. According to a further embodiment, a guard ring may be located around the ion chamber, wherein the guard ring may be charged to a guard ring voltage substantially the same as a charge voltage on the capacitor. According to a further embodiment, a second capacitor may be coupled to the capacitor.

According to another embodiment, an apparatus for detecting smoke may comprise: an ionization chamber having a radiation source and comprising first and second electrodes, wherein the ionization chamber may be open to smoke ingress; a pulse generator coupled to the first electrode of the ionization chamber, wherein the pulse generator output may comprise voltage transitions from substantially zero volts to substantially a voltage; a capacitor coupled to the second electrode of the ionization chamber; a precharge voltage reference; a precharge switch coupled between the precharge voltage reference and the capacitor, wherein the precharge switch initially couples the precharge voltage reference to the capacitor for charging the capacitor to a first voltage; a voltage determination circuit coupled to the capacitor; and a pulse counter coupled to the pulse generator and counting a number of pulses therefrom, wherein the pulse counter counts the number of pulses from the pulse generator required to charge the capacitor to a second voltage.

According to a further embodiment, the pulse generator may be a pulse width modulation (PWM) generator having programmable time periods. According to a further embodiment, the first voltage may be about one-half the voltage. According to a further embodiment, the voltage determination circuit may comprise a voltage comparator. According to a further embodiment, the voltage determination circuit may comprise an analog-to-digital converter (ADC).

According to a further embodiment, the pulse generator, the capacitor, the precharge voltage reference, the precharge switch, the voltage determination circuit, and the pulse counter may be provided in a microcontroller. According to a further embodiment, the microcontroller further may comprise an alarm driver. According to a further embodiment, an audible/visual alarm may be coupled to the alarm driver. According to a further embodiment, a guard ring may be around the ion chamber, wherein the guard ring may be charged to a guard ring voltage substantially the same as a charge voltage on the capacitor. According to a further embodiment, a second capacitor may be coupled to the capacitor.

BRIEF DESCRIPTION OF THE DRAWINGS

A more complete understanding of the present disclosure may be acquired by referring to the following description taken in conjunction with the accompanying drawings wherein.

Figure 1:
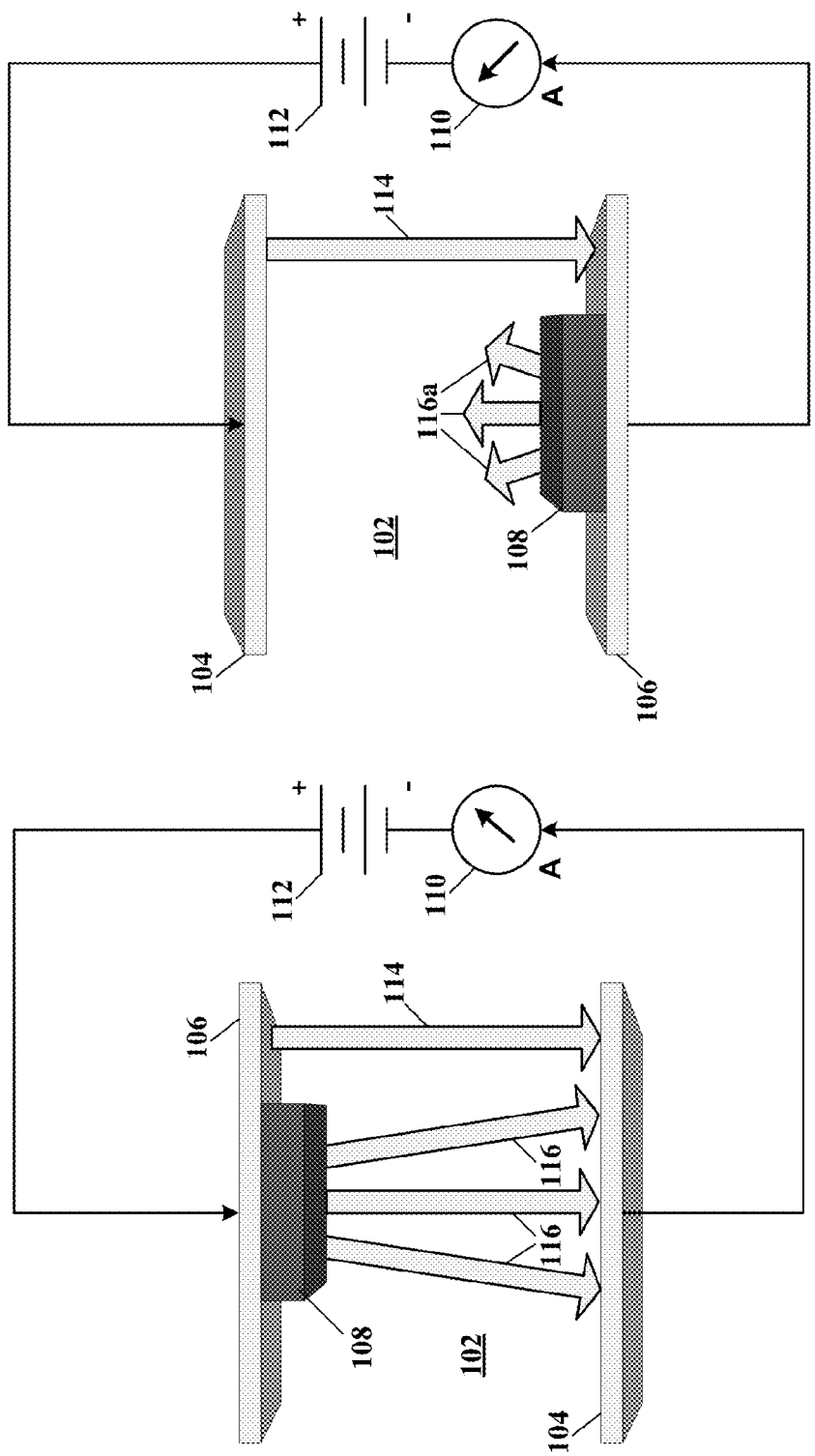
FIG. 1 illustrates schematic diagrams of an ion chamber having a radiation source and showing current flows therethrough for different polarity voltage connections thereto.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

According to embodiments of this disclosure discussed herein will allow, in particular, small currents to be directly measured with a microcontroller without external components except for a sensor having a current output, e.g., smoke detection ion chamber. An ion chamber may be modeled as a capacitor having current leakage therethrough, or a variable high resistance dependent upon the ionization of a gas in the ion chamber. Ionization of the gas is caused by an ion source in the smoke detection ion chamber. Unwanted leakage current is also present on a printed circuit board (PCB) to which the smoke detection ion chamber is coupled.

An ion chamber used for detection of smoke comprises a radioactive source in the ion chamber that causes some of the gas (e.g., air) molecules in the chamber to ionize. This results in a higher than normal permittivity of the gas due to the higher than normal number of electrically polarized (ionized) gas molecules. Therefore, when a voltage is placed across two of the ion chamber electrodes (see FIG. 1) a small current will flow through this ionized gas. When smoke enters the ion chamber, the smoke reacts with the ionized gas molecules thereby changing the permittivity, $\epsilon$, thereof, and reduces the number of ionized gas molecules. This results in a lower leakage current through the ion chamber. The ion chamber current leakage will vary with temperature, relative humidity and voltage variations. But these variations are very slow to change. However, smoke causes a sudden change in the ion chamber leakage current (reduces the ion current).

By applying a voltage potential at a first polarity across the ion chamber and measuring total current through the ion chamber and the PCB leakage current, and then applying a voltage potential at a second (opposite) polarity across the ion chamber and measuring only the PCB leakage current. The common mode bipolar PCB leakage current can be isolated from the unipolar ion current, thereby increasing the sensitivity of smoke detection in the ion chamber. In addition, costly physical leakage compensation techniques are no longer required.

A sampling capacitor used with an analog-to-digital converter (ADC) has certain constraints. However, these constraints are known. External solutions require additional amplification steps to combat parasitic affects of the equipment printed circuit board (PCB) and other environment conditions. By moving the necessary circuit parts into the microcontroller and ADC, these parasitic affects are readily known, controlled, and the circuit solution is more compact and sensitive to sensor inputs.

Such a current/voltage interface can be advantageously used with an ion chamber smoke detector and will significantly reduce the cost of interfacing to the ion chamber smoke sensor. According to various embodiments, a current from an external device such as an ion chamber is connected to an input of an ADC. The internal sampling capacitor of the ADC accepts the current charge and creates a voltage over a time period. After the time period has elapsed, the voltage on the S/H capacitor may be measured by starting a conversion from analog to digital with the ADC. Alternatively, when a certain voltage (voltage target) is reached on the S/H capacitor, the time required to charge the S/H capacitor to the certain voltage may be determined. Either way, ion current through the ion chamber smoke sensor may be determined, and a change in the ion current is indicative of smoke in the ion chamber.

This current represents gas ionization current through the ion chamber and printed circuit board leakage current when a first polarity voltage is applied to the ion chamber electrodes. When a second polarity voltage (opposite to the first polarity voltage) is applied to the ion chamber electrodes, the charging current will only be the printed circuit board leakage current. By subtracting the current determined using the second polarity voltage from the current determined using the first polarity voltage, the gas ionization current may be determined.

Portions of a Charge Time Measurement Unit (CTMU) may be used in determining the charge voltage value on the S/H capacitor. The CTMU is more fully described in Microchip applications notes AN1250, AN1375, etc., available at www.microchip.com, and U.S. Pat. Nos. 7,460,441 B2 and 7,764,213 B2; wherein all are hereby incorporated by reference herein for all purposes. The CTMU charge voltage measurement accuracy is achieved by charging a known value capacitor from a current source over a known time period, then sampling a voltage developed on the charged capacitor. This sampled voltage is then converted into a digital value with an analog-to-digital converter (ADC) and, optionally, a look-up table may be used, or other means, to convert the digital value of the sampled voltage into a value for comparison against a reference value. If the sampled voltage value is significantly different, as in an alarm condition, e.g., smoke detection, than the reference value then an alarm may be initiated. If the sampled voltage value is within desired values then no alarm condition exists.

The various embodiments described herein, provide for the ability to create a cost effective solution for applications using sensors having current outputs. Thus, the need for expensive operational amplifiers and associated circuitry is removed. An interface according to various embodiments may be advantageously used in combination with smoke detector ion chambers to detect fast occurring smoky fires.

Referring now to the drawings, the details of specific example embodiments are schematically illustrated. Like elements in the drawings will be represented by like numbers, and similar elements will be represented by like numbers with a different lower case letter suffix.

Referring to FIG. 1, depicted are schematic diagrams of an ion chamber having a radiation source and showing current flows therethrough for different polarity voltage connections thereto. The ion chamber 102 may be characterized as two electrodes, e.g., electrodes 104 and 106, having some ionized gas (e.g., air) molecules therebetween. The gas molecules are ionized by a radiation source 108. When a voltage potential 112 is applied between the two electrodes 104 and 106 at a first polarity (positive to electrode 106 and negative to electrode 104), a positively biased ionization electron current 116 will flow through the ionized gas. When the voltage potential 112 is applied between the two electrodes 104 and 106 at a second polarity (positive to electrode 104 and negative to electrode 106), substantially no negatively biased ionization electron current 116a will flow through the ionized gas since now the electrode 104 will repel the ionized gas electrons. However, leakage current 114, e.g., printed circuit board contaminates, grease, dust, etc., will flow irrespective of the connected polarity of the voltage potential 112.

Thus when the voltage potential 112 is connected at the first polarity across chamber 102 electrodes 104 and 106, the total current flow through the current meter 110 is the ionized electron current 116 plus the leakage current 114. And when the voltage potential 112 is connected at the second polarity across chamber 102 electrodes 104 and 106, the total current flow through the current meter 110 is substantially no ionized electron current 116a plus the leakage current 114 which results in substantially only the leakage current 114. Therefore, by subtracting the leakage current 114 from the total current flow, the actual ionized electron current 116 may be determined. This allows more sensitive measurements of any change in the ionized electron current 116 without these changes being masked by the undesired leakage current 114. It is contemplated and within the scope of this disclosure that any fluid, e.g., gas or liquid, that can be ionized by the ion source 108 will function as described hereinabove.

Figure 2:
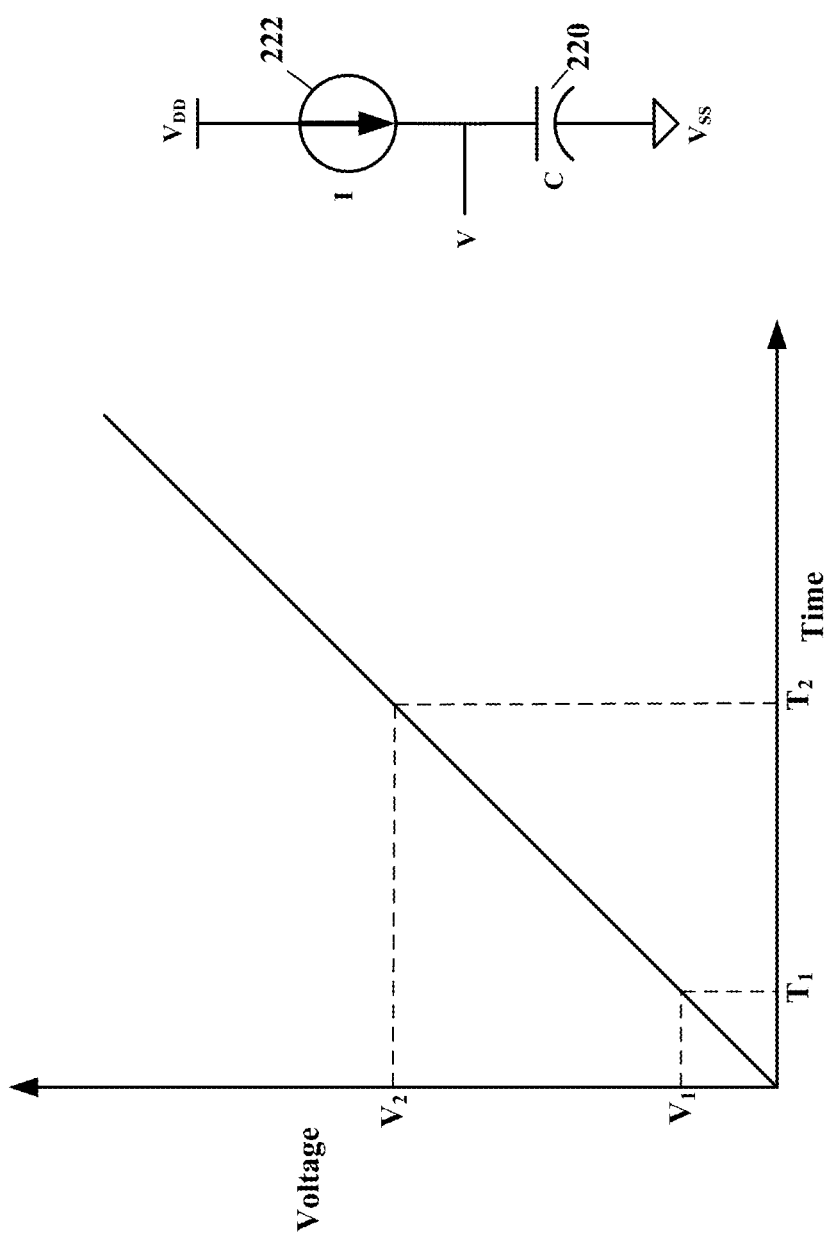
FIG. 2 illustrates a time-voltage graph of a capacitor being charged from a constant current source.

Referring to FIG. 2, depicted is a time-voltage graph of a capacitor being charged from a constant current source. When a capacitor 220 is charged through a constant current source 222 the voltage, V, across the capacitor 220 increases linearly with time, according to equation (1): $I = C \cdot dV/dT$, where C is the capacitance value of the capacitor 220, I is the current from the constant current source 222 and V is the voltage on the capacitor 220 at time T. When any two values of the current, I; time, T; and voltage, V are known, the other unknown value may be calculated from the two known values. For example, if the capacitance of the capacitor 220 and the time $T = T_2 - T_1$ are known, and the voltage V on the capacitor 220 is measured, a current charge may be determined. This allows conversion of the charge voltage (e.g., voltage on the capacitor 220) to the measured process variable, e.g., ionized electron current 116 plus leakage current 114, and substantially leakage current 114 (current 116a+current 114). A simple voltage to process variable value look-up table may also be provided and stored in a memory of a digital processor 326 (FIG. 3).

Figure 3:
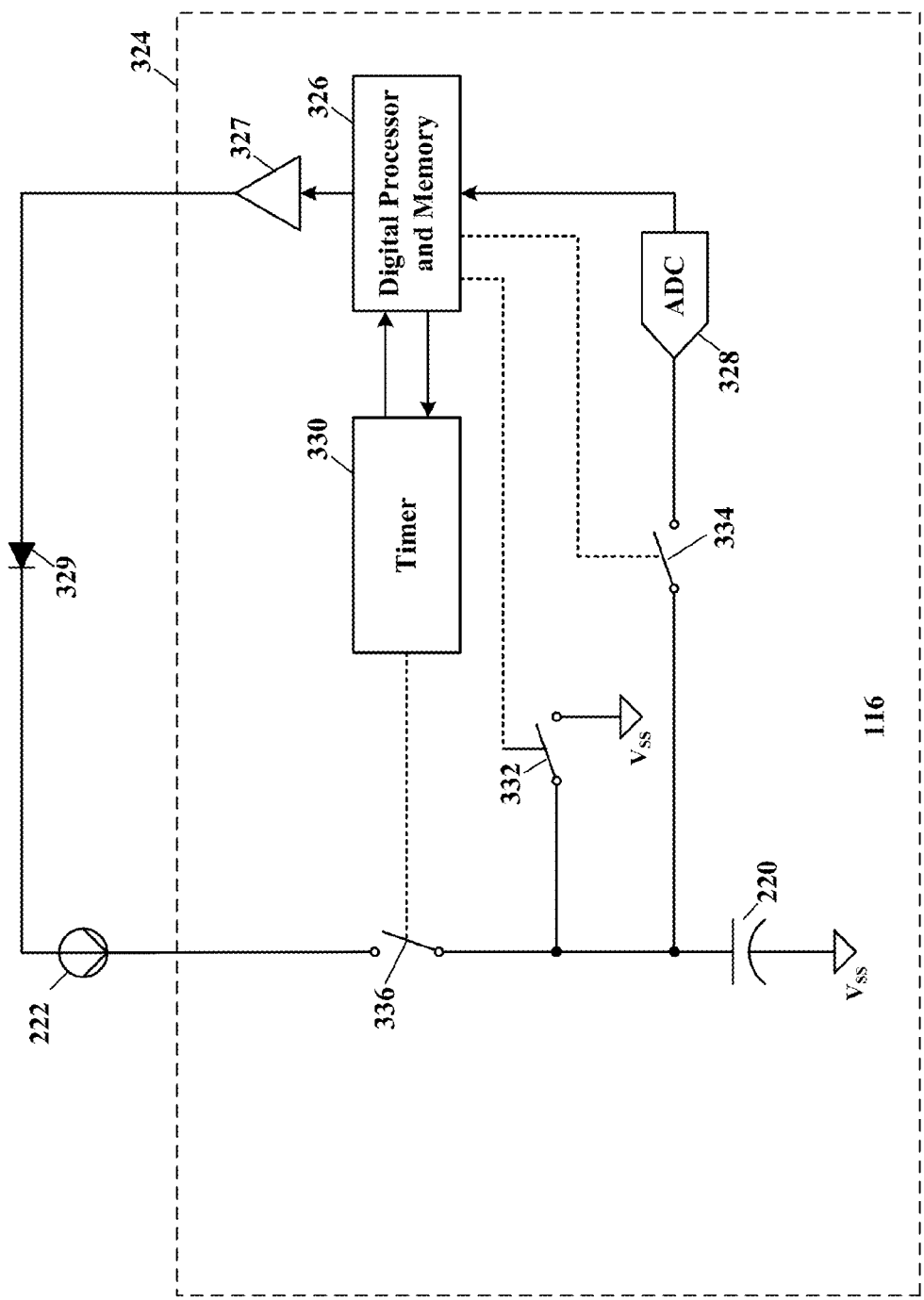
FIG. 3 illustrates a schematic block diagram of a current source coupled to input and output interfaces of a microcontroller, according to the teachings of this disclosure.

Referring to FIG. 3, depicted is a schematic block diagram of a current source coupled to input and output interfaces of a microcontroller, according to the teachings of this disclosure. The microcontroller 324 comprises an internal analog-to-digital converter (ADC) 328 having an associated sample and hold (S/H) capacitor 220. Furthermore a sample and hold switch 336 and a discharge switch 332 are provided. The discharge switch 332 discharges the S/H capacitor 220 to substantially zero (0) volts. An ADC switch 334 is provided to couple the ADC 328 to the S/H capacitor 220 during an analog-to-digital conversion cycle.

A timer 330 may be used to precisely control the sample and hold switch 336. A digital processor and memory 326 in the microcontroller 324 may be used to control the discharge switch 332 and the ADC switch 334 (or the ADC 328 peripheral may control the switch 334) and start the timer 330, or an independent control unit (not shown) may be separately provided from digital processor 326 in the microcontroller 324 to independently control the operation of charging and sampling the S/H capacitor 220. According to other embodiments, this control unit (not shown) may be, for example but is not limited to, a programmable state machine or any other suitable sequential control unit within the microcontroller 324.

The current source 222 may be a sensor having a current output, e.g., an ion smoke chamber 102 (see FIG. 1). An output driver 327 may be used to drive the current source 222, and periodically supply operating voltage 112 (FIG. 1) to the current source 222 for conservation of power, e.g., increase battery life. The ion smoke chamber 102 may also be characterized as a variable resistor having a very high resistance that changes (increases) with the introduction of smoke therein. The resulting charge voltage on the S/H capacitor 220 is a result of the RC time constant of the ion smoke chamber 102 equivalent resistance and the S/H capacitor 220 capacitance. Preferably, the output driver 327 may apply the supply operating voltage 112 over time periods that will charge the S/H capacitor 220 to voltages that will allow the best voltage resolution by the ADC 328. Furthermore the time periods may be changed for varying operating conditions to optimize the charge voltage on the S/H capacitor 220, e.g., one-half of the supply voltage during quiescent sampling conditions. Thereby maximizing the range resolution of measurable changes in charge voltage up or down from the quiescent voltage sampling conditions.

Figure 4:
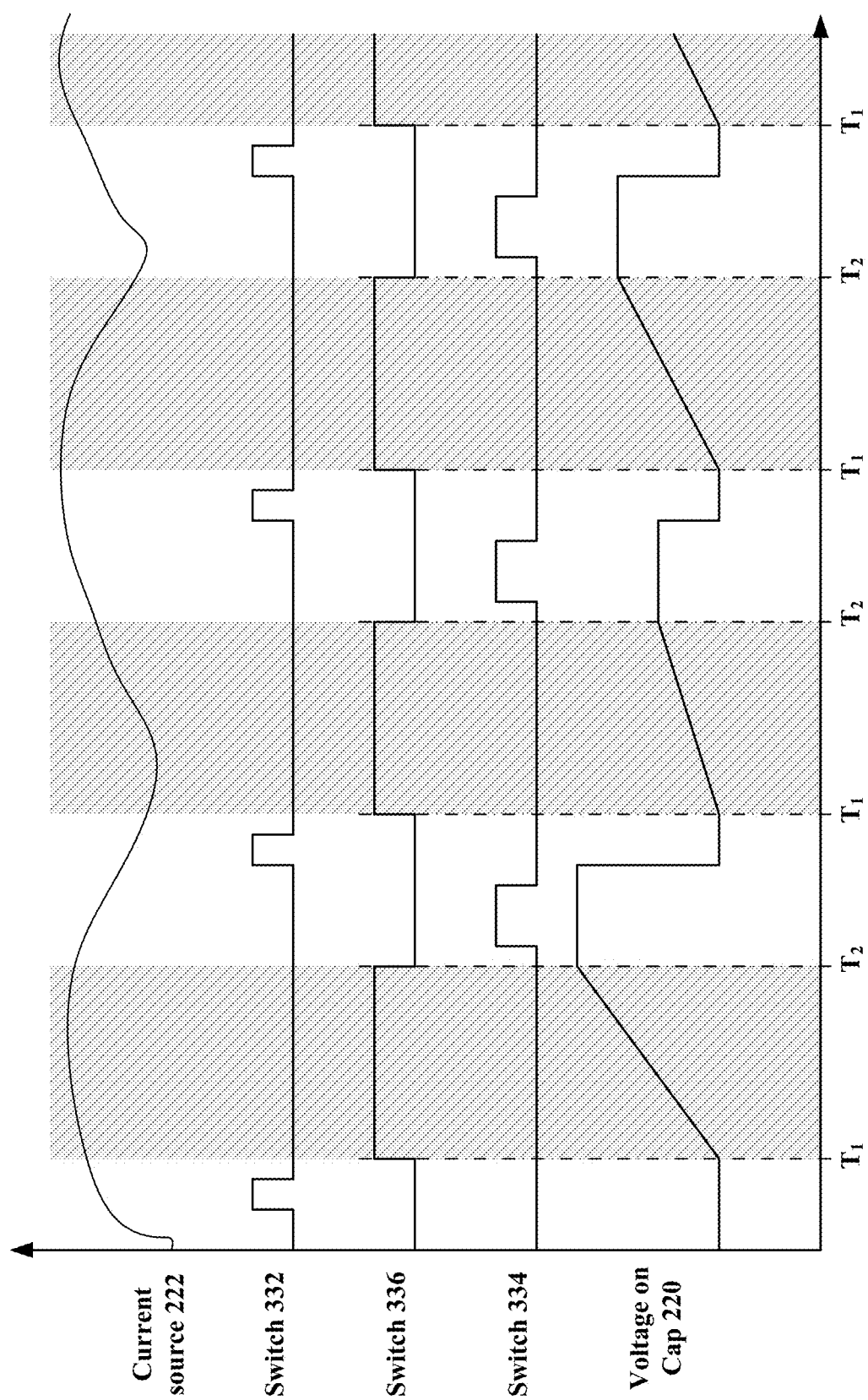
FIG. 4 illustrates schematic timing diagrams for operation of the peripheral functions shown in FIG. 3, according to the teachings of this disclosure.

Referring to FIG. 4, depicted are schematic timing diagrams for operation of the peripheral functions shown in FIG. 3, according to the teachings of this disclosure. Switch 332 closes, removing any charge on the S/H capacitor 220 to substantially zero volts. Then the timer 330 closes the sample and hold switch 336 for a know fixed period of time, $T=T_2-T_1$. Then after time T the sample and hold switch 336 opens. This causes the sample and hold capacitor 220 to be charged at a rate determined by the current source 222 driven by an output driver 327. After the time period T has elapsed, the ADC switch 334 closes and the ADC 328 converts the charge voltage on the S/H capacitor 220 to a digital representation thereof. The digital processor 326 may thereafter read this digital representation for further processing, e.g., smoke detection and alarm notification thereof. The switch 336 may be eliminated by driving the driver 327 with the output of the timer 330, and the output of the driver 327 may be in series with a bidirectional current diode 329 to prevent discharge of the S/H capacitor back into the driver 327 when in a logic low output condition. The output of the driver 327 may also be placed into a high impedance state once the pulse to the S/H capacitor 220 is finished.

Figure 5:
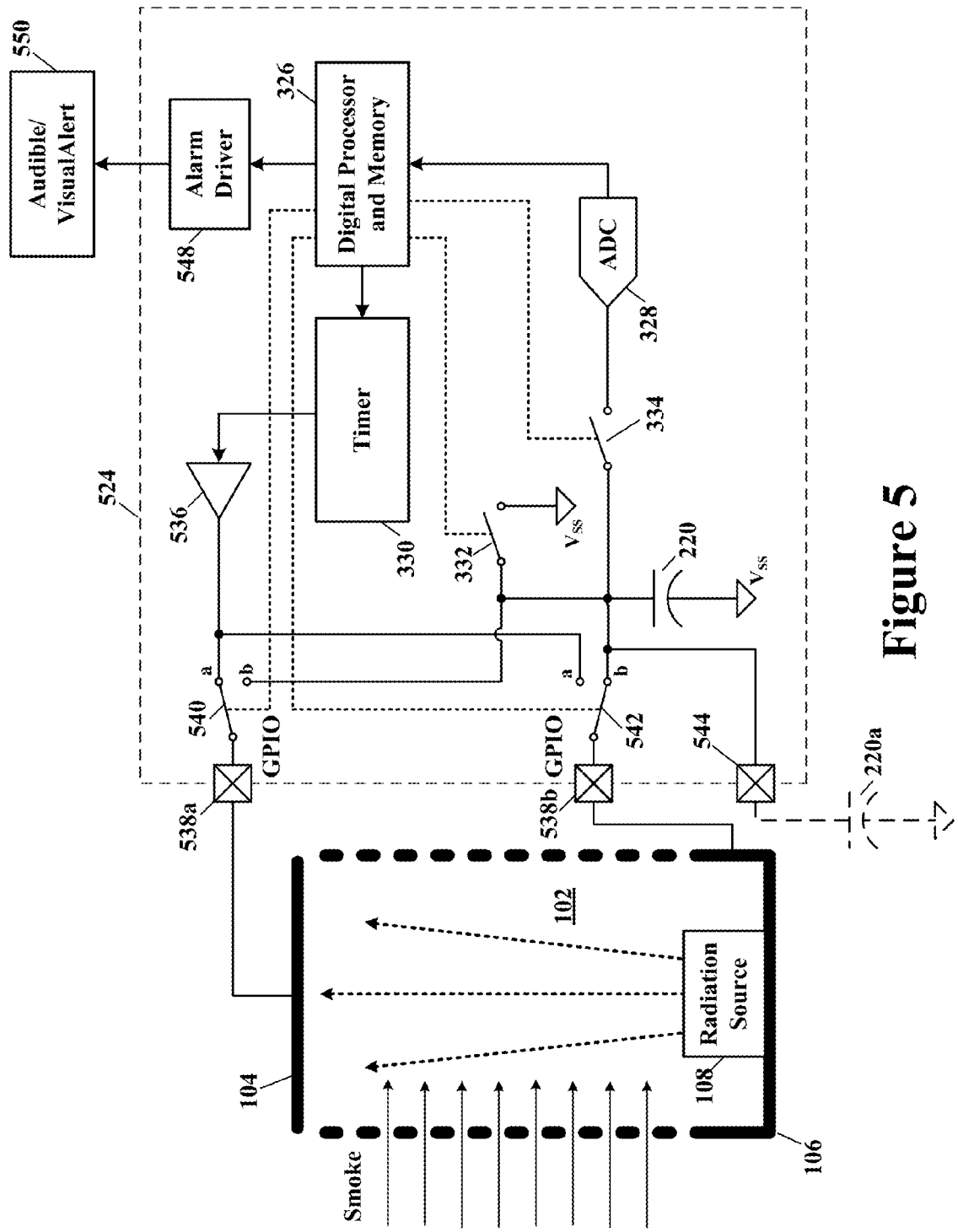
FIG. 5 illustrates a schematic block diagram of a single chamber ion smoke detector, according to a specific example embodiment of this disclosure.

Referring to FIG. 5, depicted is a schematic block diagram of a single chamber ion smoke detector, according to a specific example embodiment of this disclosure. A microcontroller 524 comprises an analog-to-digital converter (ADC) 328 having an associated sample and hold (S/H) capacitor 220, a timer 330, a digital processor and memory 326, a discharge switch 332, an ADC sample switch 334, a digital output driver 536, and general purpose input/output (GPIO) switches 540 and 542 coupled to external GPIO connections 538. The discharge switch 332 discharges the S/H capacitor 220 to substantially zero (0) volts. The ADC sample switch 334 couples the ADC 328 to the S/H capacitor 220 during an analog-to-digital conversion cycle. The microcontroller 524 may further comprise an alarm driver 548 coupled to an audible/visual alert 550, e.g., horn, siren, etc. The smoke detection ion chamber 102 is coupled to the GPIO connections 538. An external capacitor 220a may be added to input-output (I/O) connection 544 for increasing the total capacitance that the ion chamber 102 charges. This external capacitor 220a and I/O connection 544 may be added to any of the embodiments disclosed herein.

The timer 330 may be used to control a voltage pulse to the ion chamber 102. The digital processor 326 may be used to control the discharge switch 332, the ADC sample switch 334 and start the timer 330, alternatively a peripheral of the ADC 328 may control the ADC sample switch 334 and also start the timer 330, or alternatively an independent control unit (not shown) may be separately provided from the digital processor 326 to independently control the operation of these components. According to other embodiments, this control unit (not shown) may be, for example but is not limited to, a programmable state machine or any other suitable sequential control unit within the microcontroller 524. The output driver 536 applies a voltage (112) having a pulse width of a time duration determined by the timer 330, and may have a pulse duration time that may charge the capacitor 220 during quiescent operating conditions to about half of the voltage supplied from the output driver 536. Periodically generating pulses will conserve power, e.g., battery power. Between the periodic pulses, the microcontroller 524 may go into a low power sleep mode.

The GPIO switches 540 and 542 allow the electrodes 104 and 106 to be alternately connected to the output of the driver 536 and the capacitor 220. When the GPIO switch 540 is in position a, the electrode 104 is coupled through the GPIO connection 538a to the output of the driver 536. When the GPIO switch 542 is in position b, the electrode 106 is coupled through the GPIO connection 538b to the capacitor 220. In this configuration, positively biased ionization electron current 116 will flow between the electrodes 104 and 106. When the GPIO switch 540 is in position b, the electrode 104 is coupled through the GPIO connection 538a to the capacitor 220. When the GPIO switch 542 is in position a, the electrode 106 is coupled through the GPIO connection 538b to the output of the driver 536. In this configuration, negatively biased ionization electron current 116a will not flow between the electrodes 104 and 106, and the only current flow between the connections 538 will be attributable to the leakage current 114.

After the voltage pulse from the driver 536 is finished, the ADC switch 334 closes and the ADC 328 converts the charge voltage on the capacitor 220 to a digital representation thereof. This digital representation may be stored in the memory of the digital processor 326 for further processing. Alternately, converting and storing the charge voltages from the capacitor 220 when the positively biased ionization electron current 116 is flowing and then when the negatively biased ionization electron current 116a is not flowing will allow determining only the ionized electron current through the smoke detector chamber 102 by subtracting the smaller charge voltage (created by leakage current 114 only) from the larger charge voltage (created by the positively biased ionization electron current 116 and the leakage current 114).

When there is a change in the measured charge voltage that represents a smoke presence condition, the digital processor 326 can enable the alarm driver 548 that turns on the audible/visual alert 550 to indicate the presence of smoke. This change may be measured within a certain time period. A rapid rate of charge voltage change may also be used to indicate the presence of smoke, wherein a slow change in charge voltage may be caused by changes in environmental conditions, e.g., temperature, relative humidity, contaminants in air and/or on printed circuit board, etc.

Figure 6:
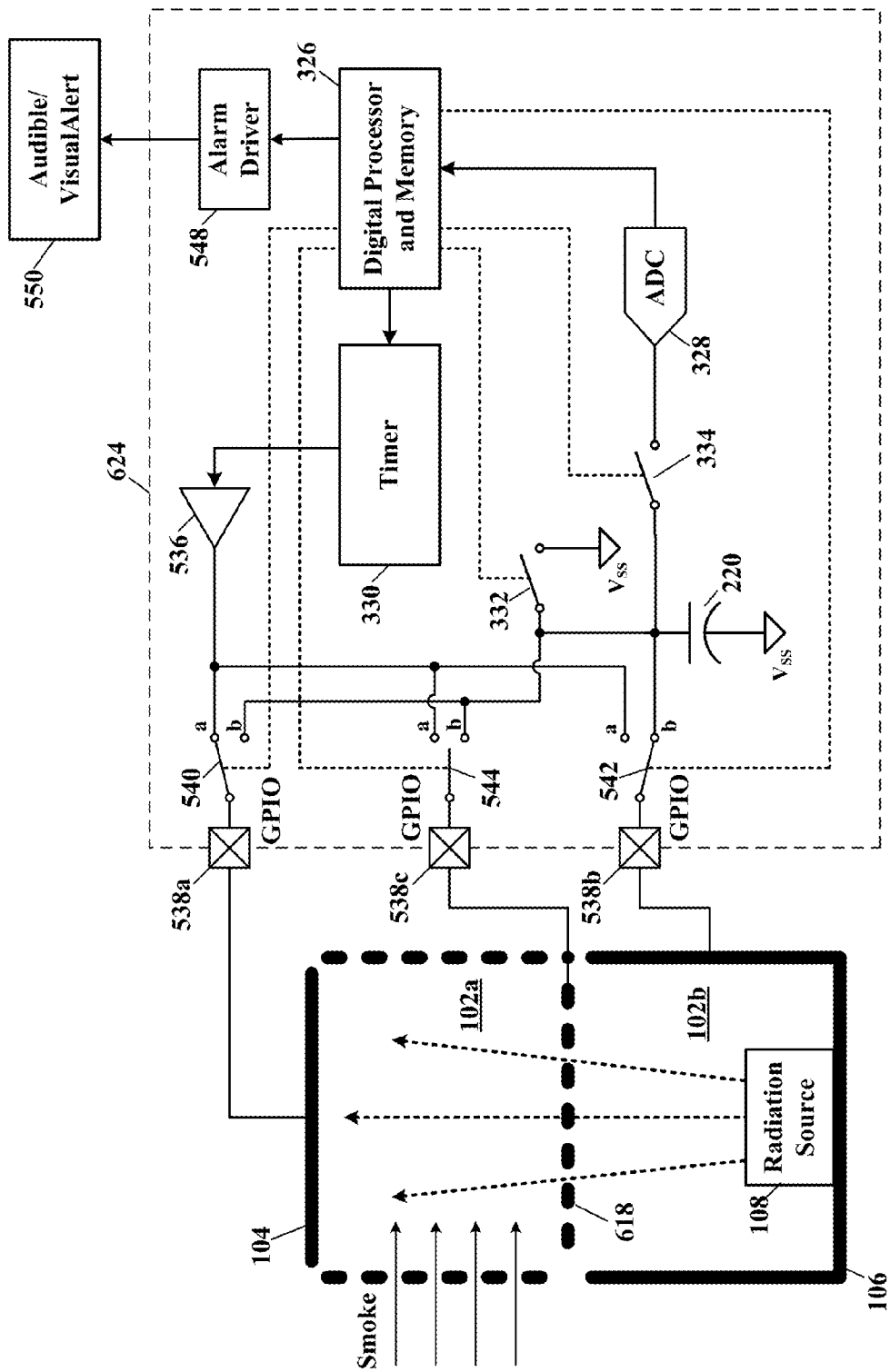
FIG. 6 illustrates a schematic block diagram of a two chamber ion smoke detector, according to a specific example embodiment of this disclosure, according to another specific example embodiment of this disclosure.

Referring to FIG. 6, depicted is a schematic block diagram of a two chamber ion smoke detector, according to a specific example embodiment of this disclosure, according to another specific example embodiment of this disclosure. The two chamber ion smoke detector works in substantially the same way as the smoke detector shown in FIG. 5 and described hereinabove with the addition of a clean air reference chamber 102b, a third GPIO connection 538c and associated GPIO switch 544. charge voltage samples may be taken as described hereinabove alternately for the smoke chamber 102a and the clean air chamber 102b, then the clean air and smoke chamber voltage samples are processed to remove any common mode leakage current, and then compared. If the difference is great enough, smoke detection is determined and the audible/visual alert 550 may be actuated.

Figure 7:
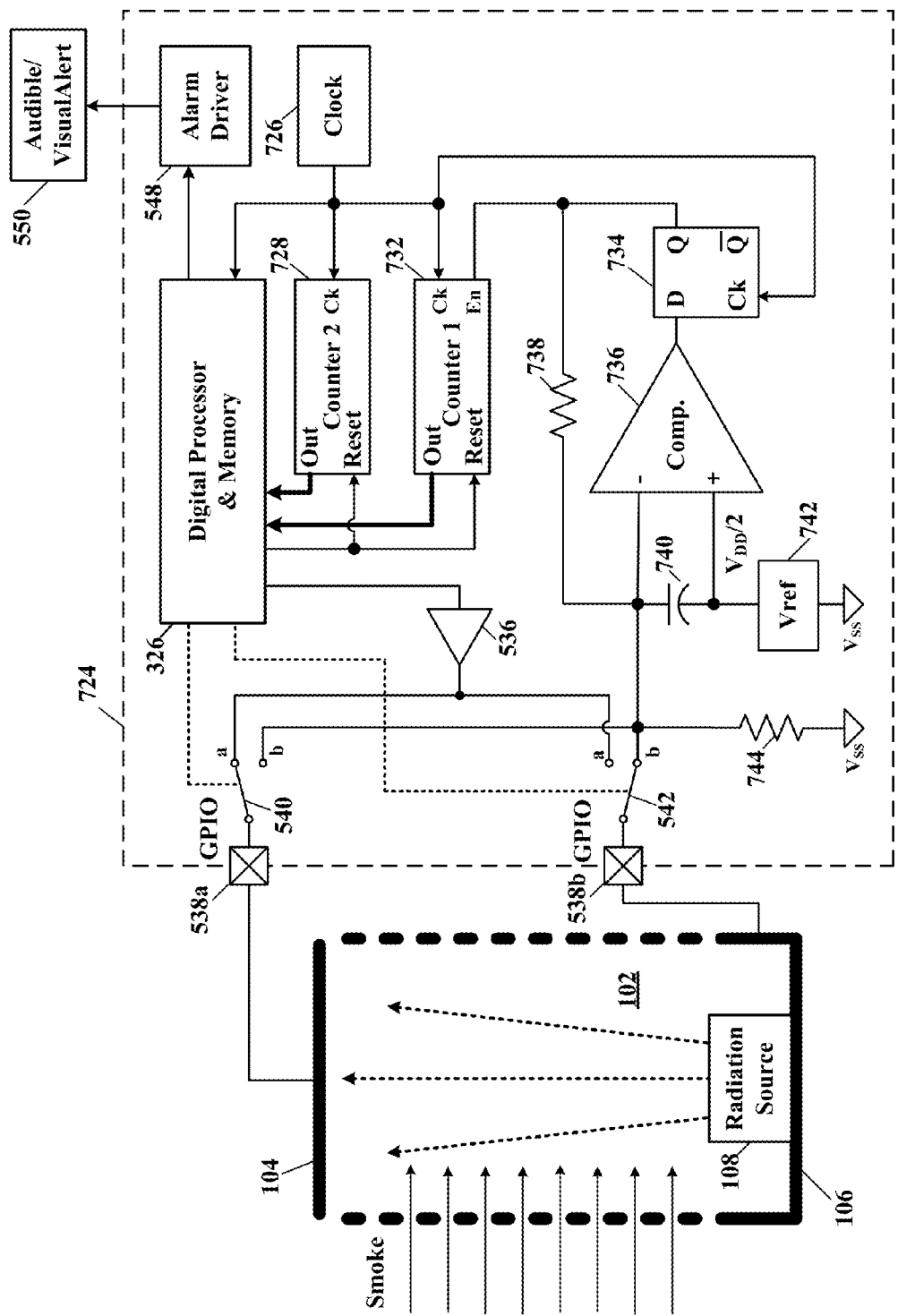
FIG. 7 illustrates a schematic block diagram of a single chamber ion smoke detector using a differential delta-sigma analog-to-digital converter (ADC), according to yet another specific example embodiment of this disclosure.

Referring to FIG. 7, depicted is a schematic block diagram of a single chamber ion smoke detector using a differential delta-sigma analog-to-digital converter (ADC), according to yet another specific example embodiment of this disclosure. A smoke detector, according to this example embodiment, may comprise a smoke detection sensor ionization chamber 102, a digital processor and memory 326, an alarm driver 548, an audible/visual alert 550, a clock generator 726, a first counter 732, a second counter 728, a voltage comparator 736, a D flip-flop 734, a feedback resistor 738, an internal capacitor 740, a voltage reference 742, and a current measurement resistor 744. All of the aforementioned elements except for the ionization chamber 102 and the audible/visual alert 550 may be provided in an integrated circuit microcontroller 724. When the digital processor 326 determines that there is smoke present, the alarm driver 548 may actuate the audible/visual alert 550, e.g., horn, siren, etc.

The ion chamber 102 electrodes 104 and 106 are coupled to GPIO connections 538a and 538b, respectively. The GPIO connections 538a and 538b are coupled to the GPIO switches 540 and 542, respectively. The GPIO switches 540 and 542 allow the electrodes 104 and 106 to be alternately connected to the output of the driver 536 and the capacitor 220. When the GPIO switch 540 is in position a, the electrode 104 is coupled through the GPIO connection 538a to the output of the driver 536. When the GPIO switch 542 is in position b, the electrode 106 is coupled through the GPIO connection 538b to the capacitor 220. In this configuration, positively biased ionization electron current 116 will flow between the electrodes 104 and 106. When the GPIO switch 540 is in position b, the electrode 104 is coupled through the GPIO connection 538a to the capacitor 220. When the GPIO switch 542 is in position a, the electrode 106 is coupled through the GPIO connection 538b to the output of the driver 536. In this configuration, negatively biased ionization electron current 116a will not flow between the electrodes 104 and 106, and the only current flow between the connections 538 will be attributable to leakage current 114.

The comparator 736 has high impedance differential inputs and a low impedance output providing logic low "0" and logic high "1" levels. The positive input of the comparator 736 may be coupled to a voltage reference 742 that may provide a reference voltage of approximately $V_{DD}/2$. Other reference voltages may be provided by the voltage reference 742 and are contemplated herein for all purposes. The capacitor 740 is coupled between the negative and positive inputs of the comparator 736. The current measurement resistor 744 provides a voltage to the positive input of the comparator 736 that is proportional to the current from the ion chamber 102. The voltage at the positive input of the comparator 736 will be at a first voltage determined by the ionization current 116 of the ion chamber 102 and the leakage current 114 when the GPIO switch 540 is in position a and the GPIO switch 542 is in position b. And to a second voltage determined by only the leakage current 114 when the GPIO switch 540 is in position b and the GPIO switch 542 is in position a.

When the voltage at the negative input of comparator 736 is greater than (or equal to) the voltage at the positive input of comparator 336 the output thereof will be at a logic "0", e.g., substantially $V_{SS}$. When the voltage at the negative input of comparator 336 is less than the voltage at the positive input of comparator 736 the output thereof will be at a logic "1", e.g., substantially $V_{DD}$.

The output of the comparator 736 is coupled to the D-input of the flip-flop 734 and every time a clock signal from the clock 726 is received at the clock input of the flip-flop 734 the logic level at the D-input will transfer to the Q-output of the flip-flop 734, e.g., substantially $V_{DD}$ or $V_{SS}$. The feedback resistor 738 is coupled between the Q-output of the flip-flop 734 and the negative input of comparator 736 which is also coupled to the top of the capacitor 740. When the Q-output of the flip-flop 734 is at a logic "1" the capacitor 740 will charge to a higher voltage, and when Q-output of the flip-flop 734 is at a logic "0" the capacitor 740 will discharge to a lower voltage. Quiescent equilibrium will be reached when the negative and positive inputs of the comparator are at substantially the same voltages. For quiescent equilibrium during no smoke being detected, the resistance of the resistor 744 selected to produce $V_{DD}/2$ and the voltage reference 742 at substantially $V_{DD}/2$, the logic I/O outputs of the flip-flop 734 will be at substantially a 50 percent duty cycle. If the voltage reference 742 output is less than $V_{DD}/2$, then the quiescent duty cycle will be less than 50 percent, and if the voltage reference 742 output is greater than $V_{DD}/2$, then the quiescent duty cycle will be greater than 50 percent. The comparator 736, flip-flop 734, feedback resistor 738 and capacitor 740 form a sigma-delta modulator.

The clock inputs of the first and second counters 732 and 728 are coupled to the clock generator 726 and increment each time a clock signal is received, except for the first counter 732 which will only increment when enabled. The enable input of the first counter 732 is coupled to the Q-output of the flip-flop 734 and its count is thereby controlled to count only when the Q-output is at one or the other logic level, e.g., at a logic "1". The maximum count values of the first and second counters 732 and 728 may be as large as necessary, e.g., 16 bits. The first and second counters 732 and 728 may also be concatenated, e.g., a plurality of first and second counters 732 and 728. The larger the count value, the greater the resolution but also an increase in the time required for analog-to-digital conversion. By applying an appropriate clock speed, and appropriate values for the feedback resistor 738, current measurement resistor 744 and capacitor 740, very high resolution may be obtained that will allow the digital processor to easily discern when there is a smoke detection event in the smoke detection ionization chamber 102.

The digital processor 326 reads the first and second count values of the first and second counters 732 and 728, respectively, then resets them to begin counting again. From the read first and second count values the digital processor 326 can determine when a smoke event has occurred. The digital processor 326 may also do decimation of these count values, averaging, etc. The digital processor 326 may also subtract the leakage current 114 from the total current (ion chamber current 116 plus leakage current 114) to remove the common mode leakage current 114 from the desired ion chamber current 116.

In addition, the digital processor 326 may perform smoothing, time averaging, noise suppression, over sampling, decimation, and/or digital signal processing to enhance the leakage current change detection sensitivity and/or reduce noise pick-up. Also a further enhancement to more reliable smoke detection is to require that the change in leakage current occurs in less than or equal to a certain time period so as to reject slow measured current changes due to variations in temperature, relative humidity and/or supply voltage (e.g., battery not shown).

It is contemplated and within the scope of this disclosure that the digital processor and memory 326 may go into a low power sleep mode while the first and second counters 732 and 728 are counting, and only wake up to read the count values therefrom and do appropriate calculations in determining whether there is smoke in the ion chamber 102. All other functions and circuits described hereinabove remain in an active mode but are all very low power. Also the second counter 728 may be a wake-up timer inherent with a low power, standby sleep mode function in a microcontroller. This sleep mode may further increase battery life of the smoke detector. The digital processor 326 may drive the driver 536 to a logic high "1" when the sigma-delta modulator is converting the voltage across resistor 744 and to a logic low "0" when the sigma-delta modulator is in a standby mode to conserve power. Samples of the smoke detector ion chamber 102 may be taken periodically for a further reduction in power consumption.

Figure 8:
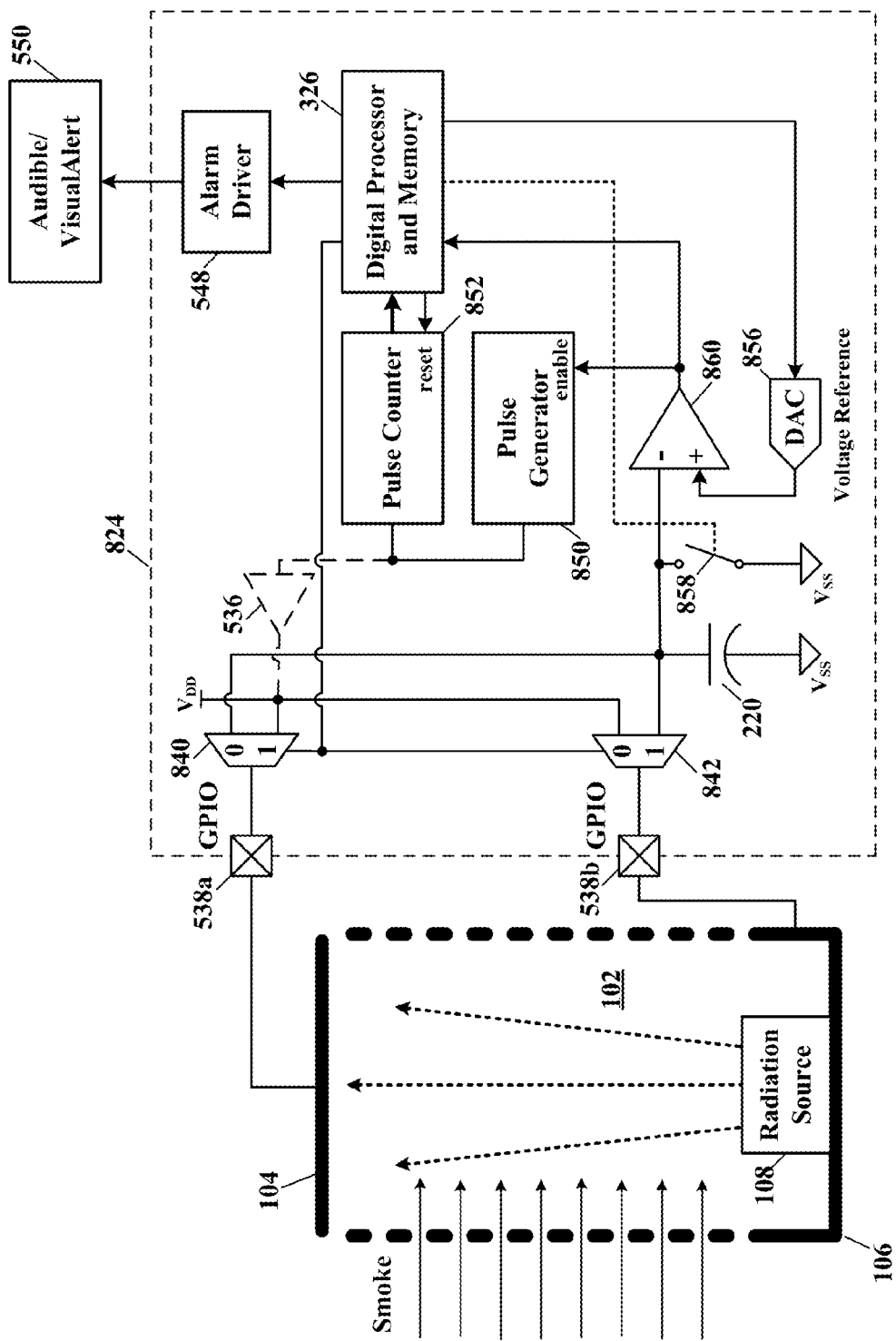
FIG. 8 illustrates a schematic block diagram of a single chamber ion smoke detector, according to still another specific example embodiment of this disclosure.

Referring to FIG. 8, depicted a schematic block diagram of a single chamber ion smoke detector, according to still another specific example embodiment of this disclosure. A microcontroller 824 comprises a pulse generator 850, a pulse counter 852, a capacitor 220, a voltage comparator 860, a voltage reference 856, a digital processor and memory 326, a discharge switch 858, and general purpose input/output (GPIO) multiplexers (switches) 840 and 842 coupled to external GPIO connections 538. The discharge switch 858 discharges the capacitor 220 to substantially zero (0) volts. The microcontroller 824 may further comprise an alarm driver 548 coupled to an audible/visual alert 550, e.g., horn, siren, etc. The smoke detection ion chamber 102 is coupled to the GPIO connections 538. The voltage reference 856 may be programmable, e.g., a digital-to-analog converter (DAC) controlled by the digital processor 326.

Optionally, a digital driver 536, having an output coupled to the multiplexer 840 instead of $V_{DD}$, may supply short duration pulses from the pulse generator 850 to the ion chamber 102 instead of a constant positive voltage, e.g., $V_{DD}$, so that the capacitor 220 takes longer to charge up to $V_{DD}$. This may allow more flexibility in the microcontroller 824 timing.

The digital processor 326 may be used to control the discharge switch 858 and reset the pulse counter 852, alternatively a peripheral may control the switch 858 and reset the pulse counter 852, or alternatively an independent control unit (not shown) may be separately provided from the digital processor 326 to independently control the operation of these components. According to other embodiments, this control unit (not shown) may be, for example, a programmable state machine or any other suitable sequential control unit within the microcontroller 824. The output driver 536 may apply voltage pulses (112) having pulse widths of time durations determined by the pulse generator 850.

Voltage (pulses) to the ion chamber 102 will charge the capacitor 220. When the charge on the capacitor 220 is greater then a reference voltage, e.g., $V_{DD}/2$, from the voltage reference 856, the output of the comparator 860 will go to a logic "0" and disable the pulse generator 850 (a logic "1" enables the pulse generator 850). The pulse counter 852 counts the number of pulses from the pulse generator 850 necessary to charge the capacitor to a certain voltage, e.g., $V_{DD}/2$. The ion chamber 102 acts as a variable current source wherein when a lower time (lower number of pulses) is required to charge the capacitor to $V_{DD}/2$ then the current through the ion chamber 102 is higher (current 116+current 114), and when a greater time (greater number of pulses) are required to charge the capacitor to $V_{DD}/2$ then the current through the ion chamber 102 is lower (current 114 only). The ion chamber 102 will have a lower current therethrough (fewer ionized gas molecules) in the presence of smoke then when no smoke is present therein.

Therefore by comparing the number of pulses required for the capacitor 220 to be charged to the certain voltage, e.g., $V_{DD}/2$, a determination can be made whether there is smoke in the ion chamber 102 or not. The digital processor 326 reads count values from the pulse counter 852, stores them in its memory, and then closes the switch 858 to discharge the capacitor 220. The cycle repeats over and over, when the GPIO multiplexers (switches) 840 and 842 are changed by the digital processor 326, as more fully described hereinafter. Periodically generating a plurality of pulses will conserve power, e.g., battery power. Between the periodic plurality of pulses, the microcontroller 824 may go into a low power sleep mode.

The GPIO multiplexers (switches) 840 and 842 allow the electrodes 104 and 106 to be alternately connected to $V_{DD}$, or alternately to the output of the driver 536, and the capacitor 220. When the GPIO multiplexer 440 is in position 0, the electrode 104 is coupled through the GPIO connection 538a to $V_{DD}$, or, alternately, to the output of the driver 536. When the GPIO multiplexer 842 is in position 1, the electrode 106 is coupled through the GPIO connection 538b to the capacitor 220. In this configuration, positively biased ionization electron current 116 will flow between the electrodes 104 and 106. When the GPIO multiplexer 840 is in position 1, the electrode 104 is coupled through the GPIO connection 538a to the capacitor 220. When the GPIO multiplexer 842 is in position 0, the electrode 106 is coupled through the GPIO connection 538b to $V_{DD}$, or alternately to the output of the driver 536. In this configuration, negatively biased ionization electron current 116a will not flow between the electrodes 104 and 106, and the only current flow between the GPIO connections 538 will be attributable to leakage current 114. The digital processor 326 may read and reset the pulse counter 852, may start and stop the pulse generator 850 for battery power conservation, and control the multiplexers (switches) 858, 840 and 842.

The number of pulses counted will be less when the positively biased ionization electron current 116 and leakage current 114 are flowing then when the negatively biased ionization electron current 116a does not flow and only the leakage current 114 charges the capacitor 20. It takes more pulses to charge the capacitor 220 to $V_{DD}/2$ when the current through the ion chamber 102 is lower. This allows determining the ionized electron current 116 through the smoke detector chamber 102 by subtracting the lower number of pulses (representative of the positively biased ionization electron current 116 and the leakage current 114) from the higher number of pulses (representative of the leakage current 114 only). The resultant difference pulse count is representative of the ionized electron current 116.

When there is a change in the resultant difference pulse count sufficient to represent a smoke presence condition, the digital processor 326 may enable the alarm driver 548 that may turn on the audible/visual alert 550 to indicate the presence of smoke. This count change may be measured within a certain time period. A rapid change of count may also be used to indicate the presence of smoke, wherein a slow change in count may only indicate changes in environmental conditions, e.g., temperature, relative humidity, contaminants in air and/or on the printed circuit board, etc.

Figure 9:
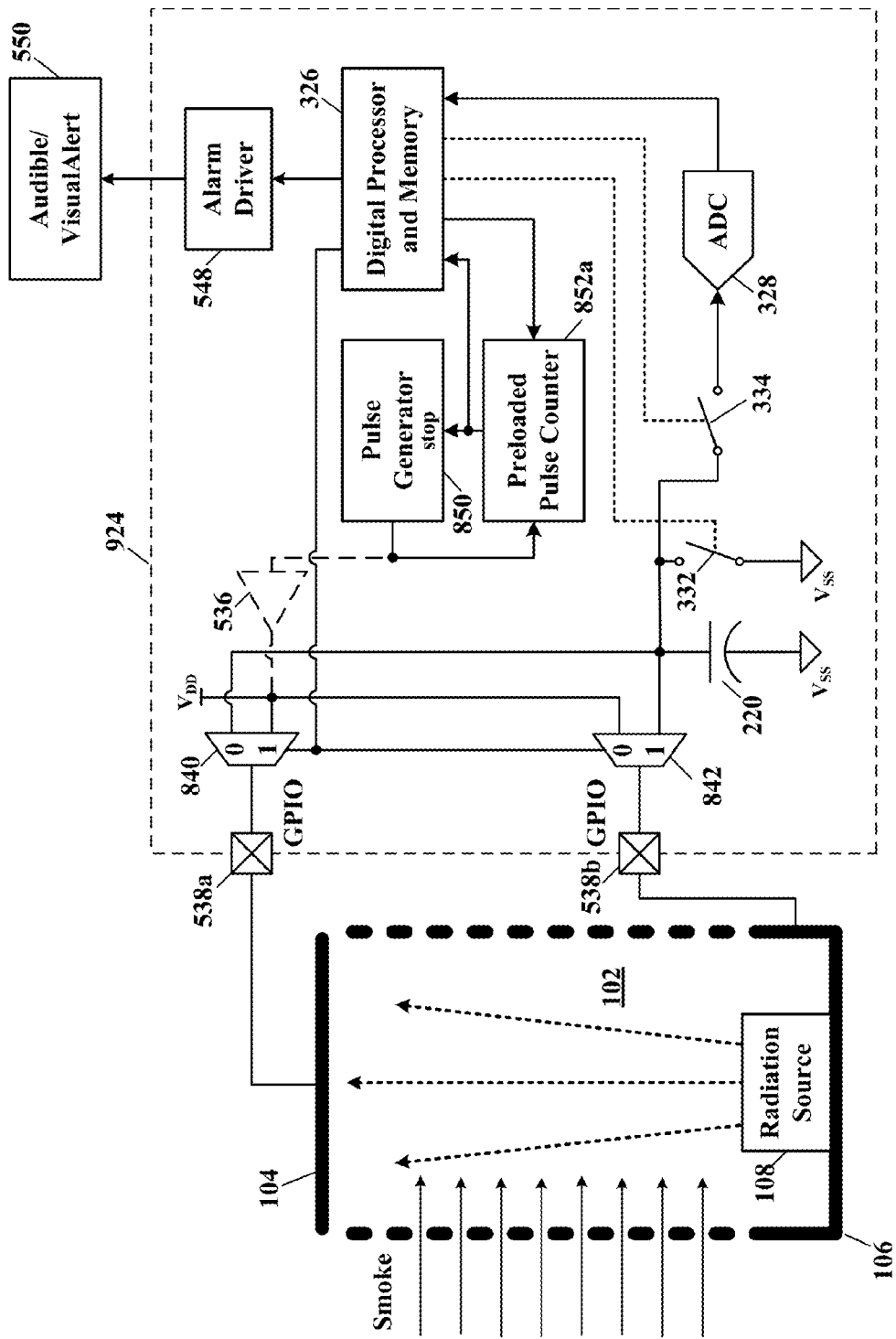
FIG. 9 illustrates a schematic block diagram of a single chamber ion smoke detector, according to yet another specific example embodiment of this disclosure.

Referring to FIG. 9, depicted is a schematic block diagram of a single chamber ion smoke detector, according to yet another specific example embodiment of this disclosure. The embodiment shown in FIG. 9 works in substantially the same way as the embodiment shown in FIG. 8 and described hereinabove, wherein an analog-to-digital converter 328 and sample switch 334 are substituted for the comparator 860 and voltage reference 856. Also the pulse counter 852a is preloaded with a certain pulse counter and will count down to zero for each plus received from the pulse generator 850. When the pulse counter 852a reaches a zero count it will stop the pulse generator 850. By selecting appropriate count values for best resolution of the voltage on the capacitor 220 by the ADC 328 very sensitive resolution of the voltage on the capacitor 220 may be converted into a counter number. The count numbers determined for the ion chamber current 116 and the leakage current 114 may thereby be compared to the count numbers determined for the reverse polarity leakage current 114 only.

Figure 10:
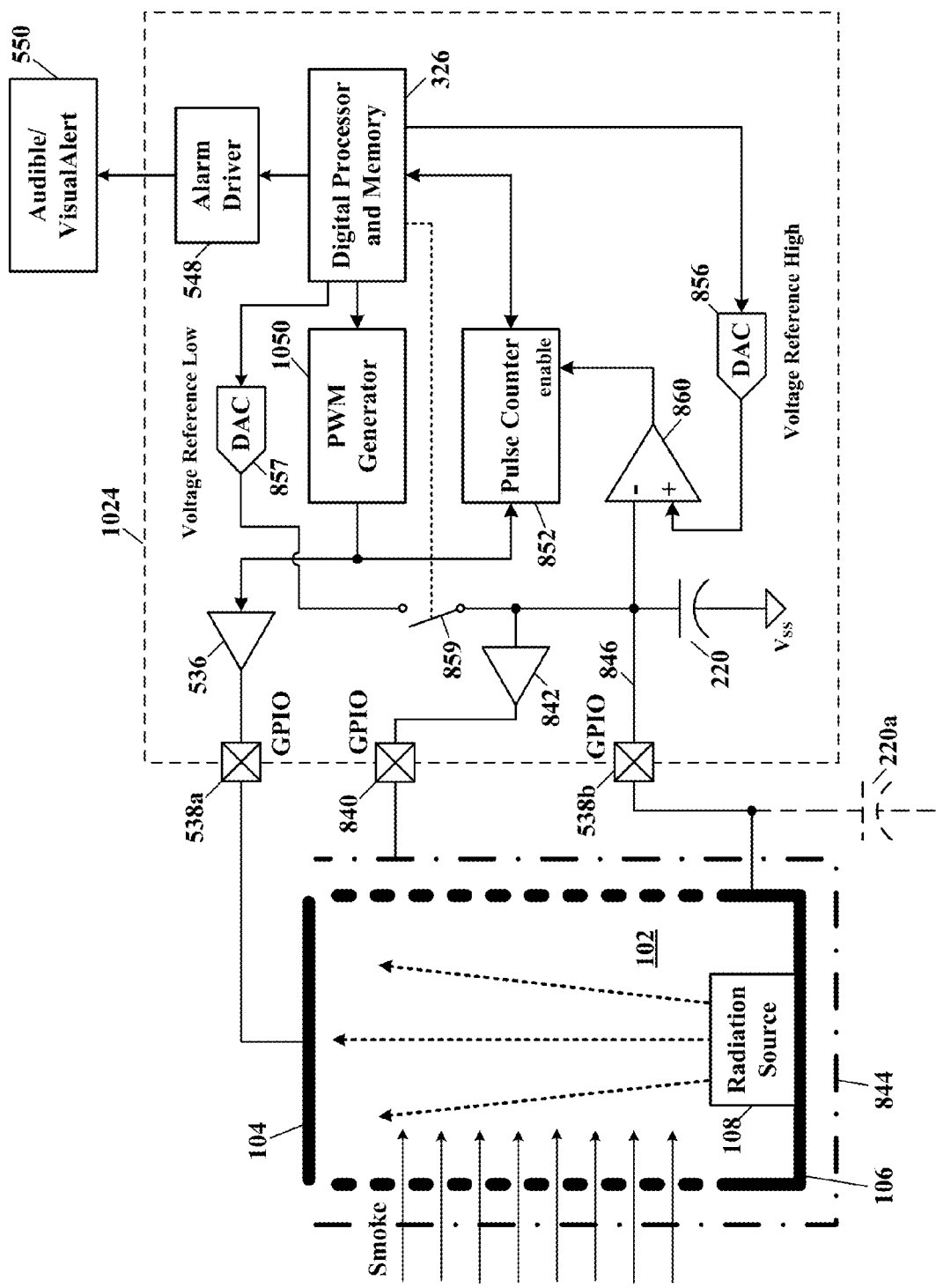
FIG. 10 illustrates a schematic block diagram of a single chamber ion smoke detector, according to another specific example embodiment of this disclosure.

Referring to FIG. 10, depicted is a schematic block diagram of a single chamber ion smoke detector, according to another specific example embodiment of this disclosure. A microcontroller 1024 comprises a pulse width modulation (PWM) generator 1050, a pulse counter 852, a capacitor 220, a voltage comparator 860, a first voltage reference 856, a second voltage reference 857, a digital processor and memory 326, a precharge switch 859, and a digital output driver 536. The precharge switch 859 charges the capacitor 220 to a nominal positive second reference voltage, e.g. $V_{DD}/2$, from the second voltage reference 857. The microcontroller 1024 may further comprise an alarm driver 548 coupled to an audible/visual alert 550, e.g., horn, siren, etc. The smoke detection ion chamber 102 is coupled to the GPIO connections 538. The first and second voltage references 856 and 857, respectively, may be programmable, e.g., digital-to-analog converters (DACs) controlled by the digital processor 326, or may be fixed in output voltage values. The first reference voltage output from the first voltage reference 856 is greater than the second reference voltage output from the second voltage reference 857.

The PWM generator 1050 may provide at, for example but is not limited to, substantially 50 percent duty cycle pulses through the driver 536 to the ion chamber 102, or any percent combination of duty cycles described more fully hereinafter. The digital processor 326 may be used to control the precharge switch 859 and start the PWM generator 1050, alternatively a peripheral may control the precharge switch 859 and also start the PWM generator 1050, or alternatively an independent control unit (not shown) may be separately provided from the digital processor 326 to independently control the operation of these components. According to other embodiments, this control unit (not shown) may be, for example, a programmable state machine or any other suitable sequential control unit within the microcontroller 824. The output driver 536 applies high and low logic levels, e.g., $V_{DD}$ and $V_{SS}$ voltage potentials to the electrode 104 of the ion chamber 102 at selectable (programmable) duty cycles. The other electrode 106 is coupled to the capacitor 220 that has been precharged to the second reference voltage at, for example but is not limited to, $V_{DD}/2$ through the precharge switch 859.

When the voltage pulses to the electrode 104 of the ion chamber 102 are at a logic high ($V_{DD}$) the electrode 104 will be at a positive potential with respect to the electrode 106 coupled to the capacitor 220 at the second reference voltage at, for example but is not limited to, $V_{DD}/2$. The combination of the ionization current 116 and the leakage current 114 will thereby charge the capacitor 220 to a more positive voltage. When the voltage pulses to the electrode 104 of the ion chamber 102 are at a logic low ($V_{SS}$) the electrode 104 will be at a negative potential with respect to the electrode 106 coupled to the capacitor 220 at the second reference voltage at, for example but is not limited to, $V_{DD}/2$. Therefore only the leakage current 114 will discharge the capacitor 220 to a less positive voltage. Since the voltage pulses from the driver 536 may have, for example but is not limited to, about a 50 percent duty cycle, the logic high portions of the pulses will continue to charge the capacitor 220 more positively than the logic low portions of the pulses will discharge the capacitor 220. Eventually the charge voltage on the capacitor 220 will reach a positive potential approaching $V_{DD}$, because the logic high current (current 116+current 114) through the ion chamber 102 will be greater than the logic low current (current 114 only) through the ion chamber 102 flowing in the opposite direction (see FIG. 1). With no smoke present in the ion chamber 102, the ionization current 116 will be at its maximum and the capacitor 220 will charge to the positive potential approaching $V_{DD}$ in less counts then when there is smoke in the ion chamber 102 since the ionization current 116 will thereby be reduced (fewer ionized gas molecules). By determining the number of pulses required to charge the capacitor 220 to the positive potential approaching $V_{DD}$ within a certain time period, or the time required (timer not shown) to charge the capacitor 220 to the positive potential approaching $V_{DD}$, detection of smoke in the ion chamber 102 may be reliably accomplished. Very sensitive detection of the presence of smoke is accomplished by removal of the common mode leakage current 114 from being a factor in charging the capacitor 220 to the positive voltage potential approaching $V_{DD}$.

The digital processor 326 reads count values from the pulse counter 852, stores them in its memory, and then closes the switch 859 to precharge the capacitor 220. The cycle repeats over and over. Periodically generating a plurality of pulses will conserve power, e.g., battery power. Between the periodic plurality of pulses, the microcontroller 1024 may go into a low power sleep mode.

Figure 11:
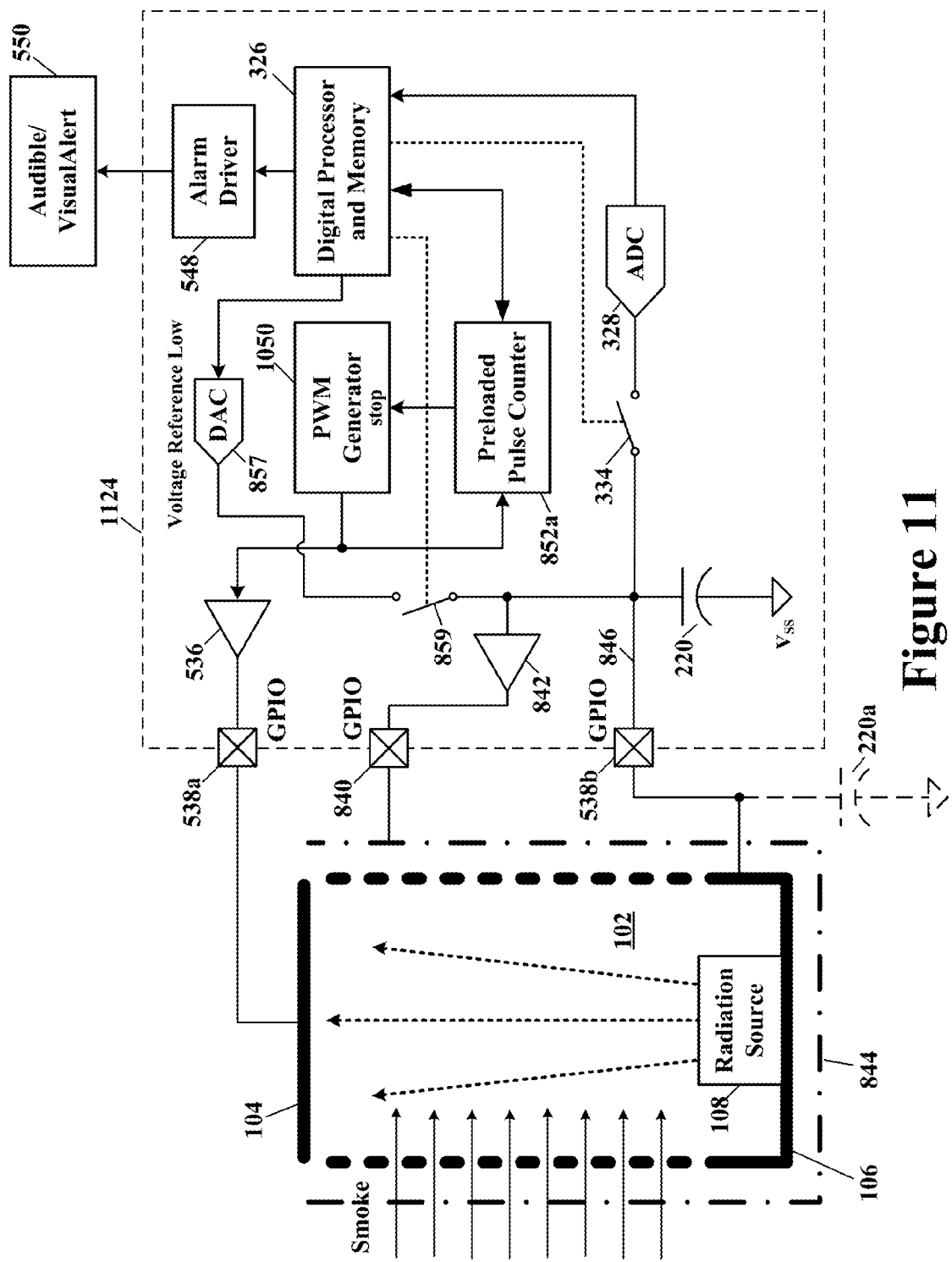
FIG. 11 illustrates a schematic block diagram of a single chamber ion smoke detector, according to still another specific example embodiment of this disclosure.

Referring to FIG. 11, depicted is a schematic block diagram of a single chamber ion smoke detector, according to still another specific example embodiment of this disclosure. The embodiment shown in FIG. 11 works in substantially the same way as the embodiment shown in FIG. 10 and described hereinabove, wherein an analog-to-digital converter 328 and sample switch 334 are substituted for the comparator 860 and voltage reference 856. Also the pulse counter 852a is preloaded with a certain pulse count and will count down to zero for each logic high pulse received from the PWM generator 1050. When the pulse counter 852a reaches a zero count it will stop the PWM generator 1050.

By selecting appropriate count values for best resolution by the ADC 328 of the positive potential approaching $V_{DD}$ on the capacitor 220, and, optionally, the precharge voltage from the DAC 857, very sensitive resolution of any change in the count number will indicate smoke in the ion chamber. Very sensitive detection of the presence of smoke is thereby accomplished by removal of the common mode leakage current 114 from being a factor in charging the capacitor 220 to the positive potential approaching $V_{DD}$.

It is contemplated and within the scope of this disclosure that the duty cycle of the pulse train from the PWM generator 1050 may change in proportion to the charge voltage on the capacitor 220. For example, when the charge voltage on the capacitor is 50% of $V_{DD}$ ($V_{DD}/2$), the duty cycle of the pulse train may be optimized at 50%. When the charge voltage on the capacitor 220 is greater than 50% of $V_{DD}$ ($V_{DD}/2$), the positive portion of the pulse train may also be greater then 50% and the zero (Vss) portion may be less than 50% since the voltage difference between the charge voltage on the capacitor 220 and $V_{DD}$ will be less then the voltage difference between the charge voltage on the capacitor 220 and Vss, so the longer pulse period at $V_{DD}$ would proportionally charge the capacitor at the smaller voltage differential. In this way the precharge voltage can be selected at any voltage value (for greater resolution accuracy) and the pulse stream duty cycle proportionally adjusted as the charge voltage on the capacitor 220 increases to $V_{DD}$. The time rate of change of the charge voltage (pulses per sample time period) on the capacitor 220 may be used in determining smoke detection in the chamber.

An external charging capacitor 220a may be added at the GPIO connection 538b to increase the capacitance valve of the capacitance 220. This will increase the time required to charge the capacitor 220 to a positive voltage approaching $V_{DD}$, thereby increasing the number of pulse counts that may be used in determining whether smoke has entered the ion chamber 102.

Figure 12:
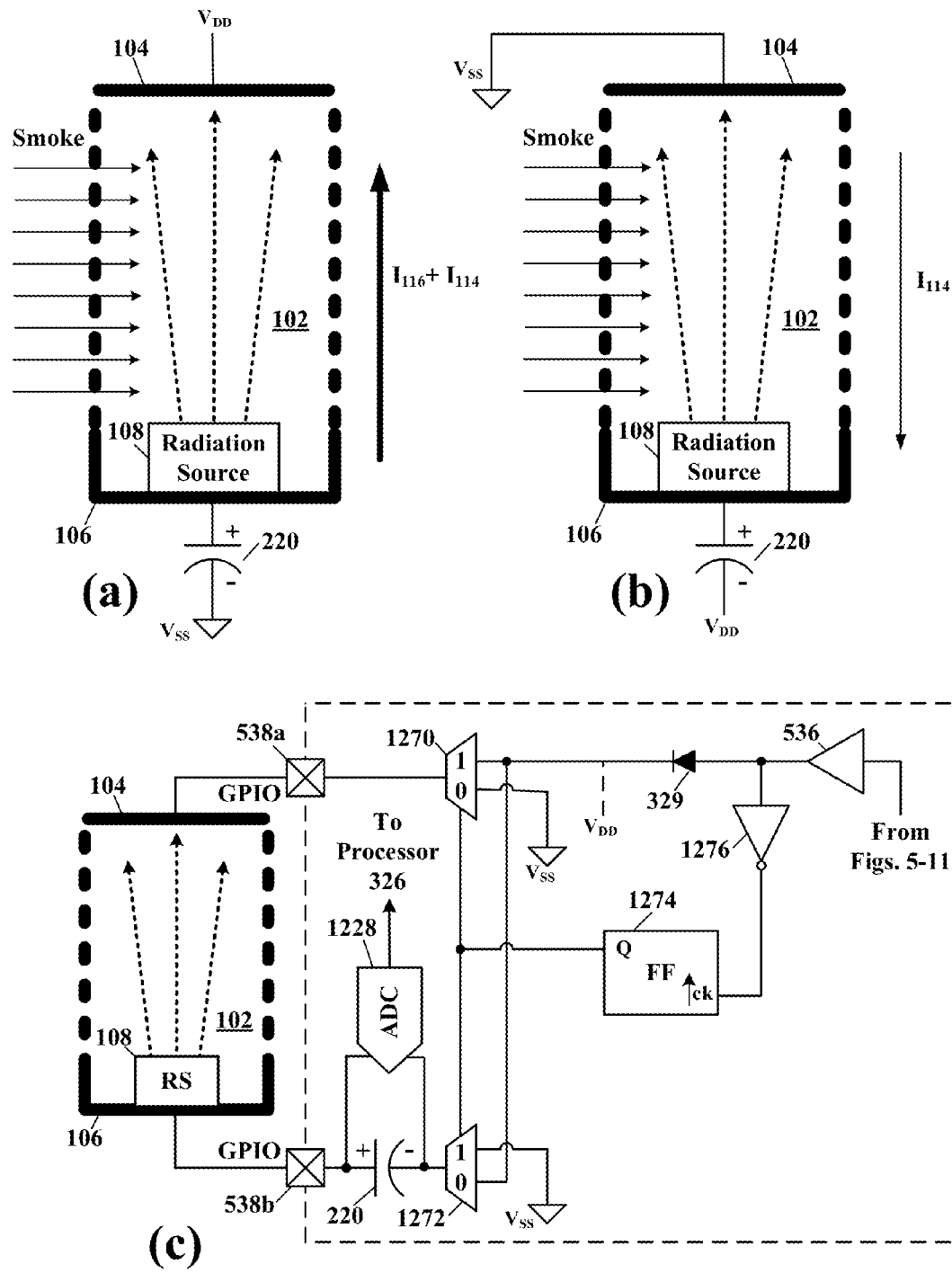
FIG. 12 illustrates a schematic block diagram of a front end portion of a single chamber ion smoke detector that may be used in combination with the embodiments disclosed and described herein, according to specific example embodiments and teachings of this disclosure.

Referring to FIG. 12, depicted is a schematic block diagram of a front end portion of a single chamber ion smoke detector that may be used in combination with the embodiments disclosed and described herein, according to specific example embodiments and teachings of this disclosure. Referring to FIG. 12(a), the ion chamber 102 is coupled in series with a capacitor 220 wherein a positive voltage, e.g., $V_{DD}$, is coupled to the electrode 104 and a common, e.g., $V_{SS}$, is coupled to a side of the capacitor 220 not coupled to the electrode 106 of the ion chamber 102. In this configuration both ionization electron current 116 and leakage current 114 charge the capacitor 220 to a positive voltage on the side of the capacitor 220, represented by a "+," that is coupled to electrode 106 of the ion chamber 102.

Referring to FIG. 12(b), the ion chamber 102 is coupled in series with the capacitor 220 wherein the common, e.g., $V_{SS}$, is coupled to the electrode 104 and the positive voltage, e.g., $V_{DD}$, is coupled to the side of the capacitor 220 not coupled to the electrode 106 of the ion chamber 102. In this configuration only the leakage current 114 discharges the capacitor 220 to a less positive voltage. In effect, the polarity of the voltage coupled to the series coupled ion chamber 102 and capacitor 220 are reversed between the configurations shown in FIGS. 12(a) and 12(b). Thus when the capacitor 220 and the ion chamber 102 are configured as shown in FIG. 12(a) the capacitor 220 is charged at a higher current (ion current 116+leakage current 114) than when configured as shown in FIG. 12(b) in which the capacitor 220 is discharged at the lower leakage current 114. The resulting charge on the capacitor 220 is substantially from the ion current 116 only since the leakage current 114 has been effectively eliminated by alternately charging and discharging the capacitor 220 over a certain time period.

The positive voltage may be a continuous voltage, e.g., $V_{DD}$, or may be pulses having fixed or variable time durations, e.g., pulse widths. Using pulses having short time durations for the positive voltage will require a longer time to charge the capacitor 220 before it has to be discharged, e.g., by a switch 332. Variable duration pulses, e.g., pulse width modulation (PWM), may further be used to linearize the charge/discharge rates of the capacitor 220. When the charge voltage is less than ½ $V_{DD}$ a longer pulse duration may be used to discharge the capacitor 220 and a shorter pulse duration may be used to charge the capacitor for a certain time rate of voltage change. When the charge voltage is about ½ $V_{DD}$ then substantially equal pulse durations will produce about the same charge and discharge time rates of voltage change. When the charge voltage is greater than ½ $V_{DD}$ then a shorter pulse duration may be used to discharge the capacitor 220 and a longer pulse duration may be used to charge the capacitor 220.

The circuit shown in FIG. 12(c) is a circuit embodiment implementing the aforementioned voltage polarity reversals across the series coupled ion chamber 102 and capacitor 220. This circuit may be used with any of the embodiments shown in FIGS. 5-11, according to the teachings of this disclosure. In addition, no memory storage of the charge voltages resulting from a first charge voltage sample taken at the charge rate of the ion current 116 and leakage current 114, and a second charge voltage sample taken at a charge rate of only the leakage current 114 is needed, thus significant savings in digital logic overhead. The circuit shown in FIG. 12(c) performs the common mode rejection of the leakage current 114 at every other pulse from the digital output driver 536.

Multiplexers 1270 and 1272 control the voltage polarities applied to the series coupled ion chamber 102 and capacitor 220. When the Q output of flip-flop 1278 is at a logic "0" the ion chamber 102 and the capacitor 220 are coupled to a first voltage polarity as shown in FIG. 12(a). When the Q output of flip-flop 1278 is at a logic "1" the ion chamber 102 and the capacitor 220 are coupled to a second voltage polarity as shown in FIG. 12(b). The Q output of the flip-flop 1278 changes at each negative going transition of the pulses from the driver 536. Therefore, the configuration shown in FIG. 12(a) receives one pulse that charges the capacitor 220 at the ionization current 116 and leakage current 114, and the configuration shown in FIG. 12(b) receives one pulse that discharges the capacitor 220 at the leakage current 114.

This charging/discharging of the capacitor 220 goes on for a plurality of pulses until the capacitor 220 reaches a certain positive voltage, a sample may be taken thereof with an analog-to-digital converter (ADC) 1228, and then the capacitor 220 may be discharged, e.g., with a switch 332, thereafter. Voltage samples may be periodically taken, e.g., see FIGS. 5, 6, 9 and 11, and the pulse widths (PWM) of the pulses may be adjusted accordingly. A constant voltage, $V_{DD}$, may be substituted for the pulses from the driver 536 through the diode 329. The diode 329 may be used to prevent back discharging of the capacitor 220 when the pulses are at a logic low "0", e.g., common voltage. It is contemplated and within the scope of this disclosure that a guard ring 844 and analog driver 842 may be added to the circuit embodiment shown in FIG. 12(c).

Figure 13:
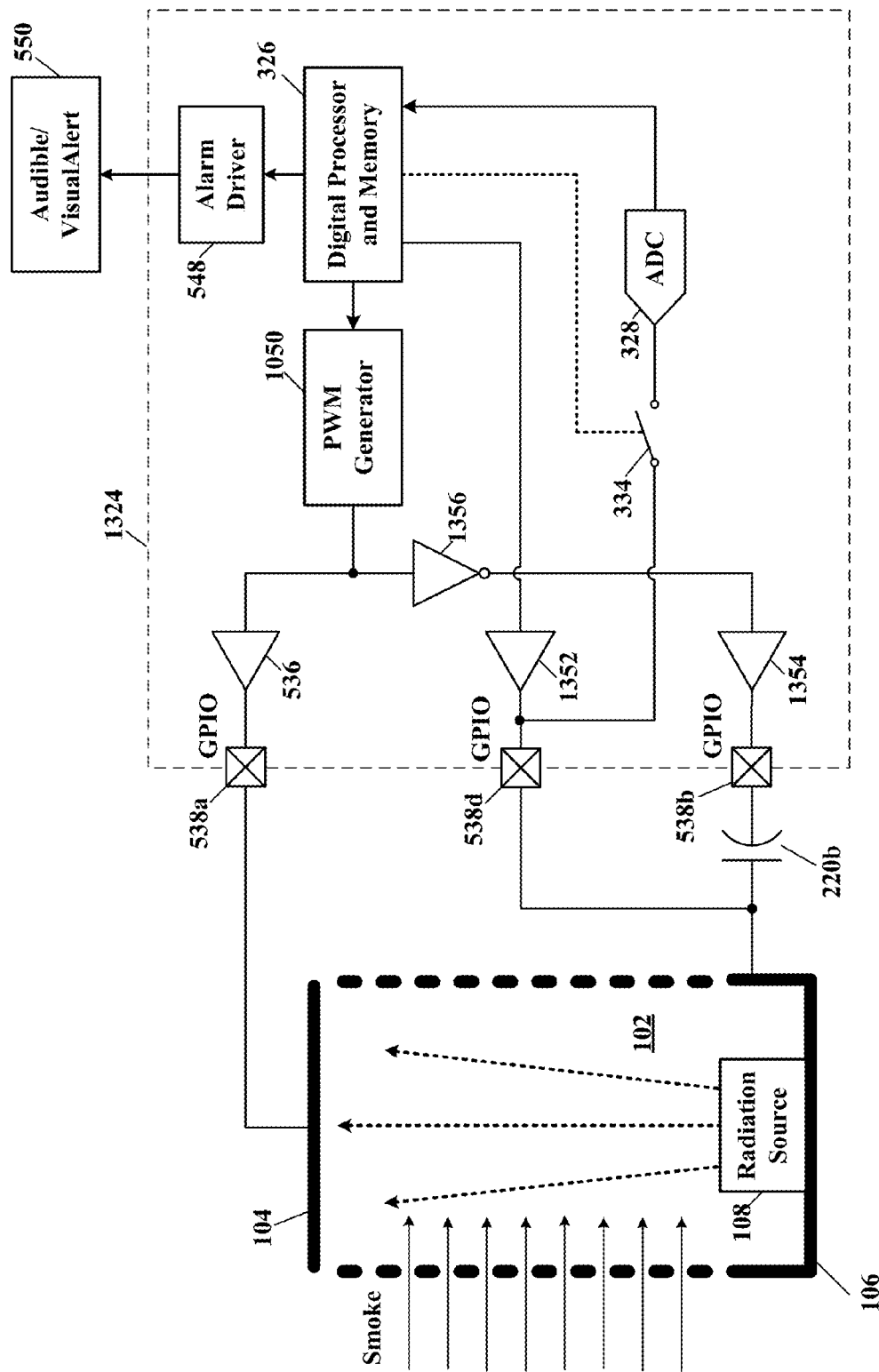
FIG. 13 illustrates a schematic block diagram of a single chamber ion smoke detector using an external charging capacitor, according to yet another specific example embodiment of this disclosure.

Referring to FIG. 13, depicted is a schematic block diagram of a single chamber ion smoke detector using an external charging capacitor, according to yet another specific example embodiment of this disclosure. The circuit shown in FIG. 13 is a very simple, mostly digital microcontroller 1324 coupled to an external capacitor 220b in combination with the ion chamber 102. Voltage polarities on the electrode 104 and the capacitor 220b coupled in series with the electrode 106 are established with digital output drivers 536 and 1354, wherein the logic level output from driver 536 is opposite the logic level output from driver 1354. Therefore, when there is a logic high from the driver 536 to the GPIO connection 538a the electrode 104 is at a positive voltage, e.g., $V_{DD}$, and the end of the capacitor 220b coupled to the GPIO connection 538b is at substantially zero (0) volts, e.g., $V_{SS}$, (see FIG. 12(a)). An inverter 1356 drives the digital output driver 1354 to a logic level opposite that of the digital output driver 536.

A pulse generator 1050, e.g., pulse width modulation (PWM) generator, provides pulses have defined pulse widths to the GPIO connections 538a and 538b. Using a PWM generator 1050 allows varying the high and low pulse widths (duty cycle) according to the value of the charge voltage on the capacitor 220b. As described more fully hereinabove, the duty cycle of the pulse train from the PWM generator 1050 may change in proportion to the change in the charge voltage on the capacitor 220b.

A digital output driver 1352 may be used to discharge the capacitor 220b then go into a high impedance output state, e.g., tri-state, so that the ADC 328 can sample the charge voltage on the capacitor 220b when the sample switch 334 is closed. The ADC 328 and switch 334 may periodically sample the changing charge voltages on the capacitor 220b and convert these voltage samples into digital representations thereof. The digital processor 326 reads these digital representations and may use them in determining whether smoke has entered the ion chamber 102, as more fully described herein. The digital processor 326 may also control the PWM generator to vary the pulse width duty cycle based upon the sampled charge voltage values.

Figure 14:
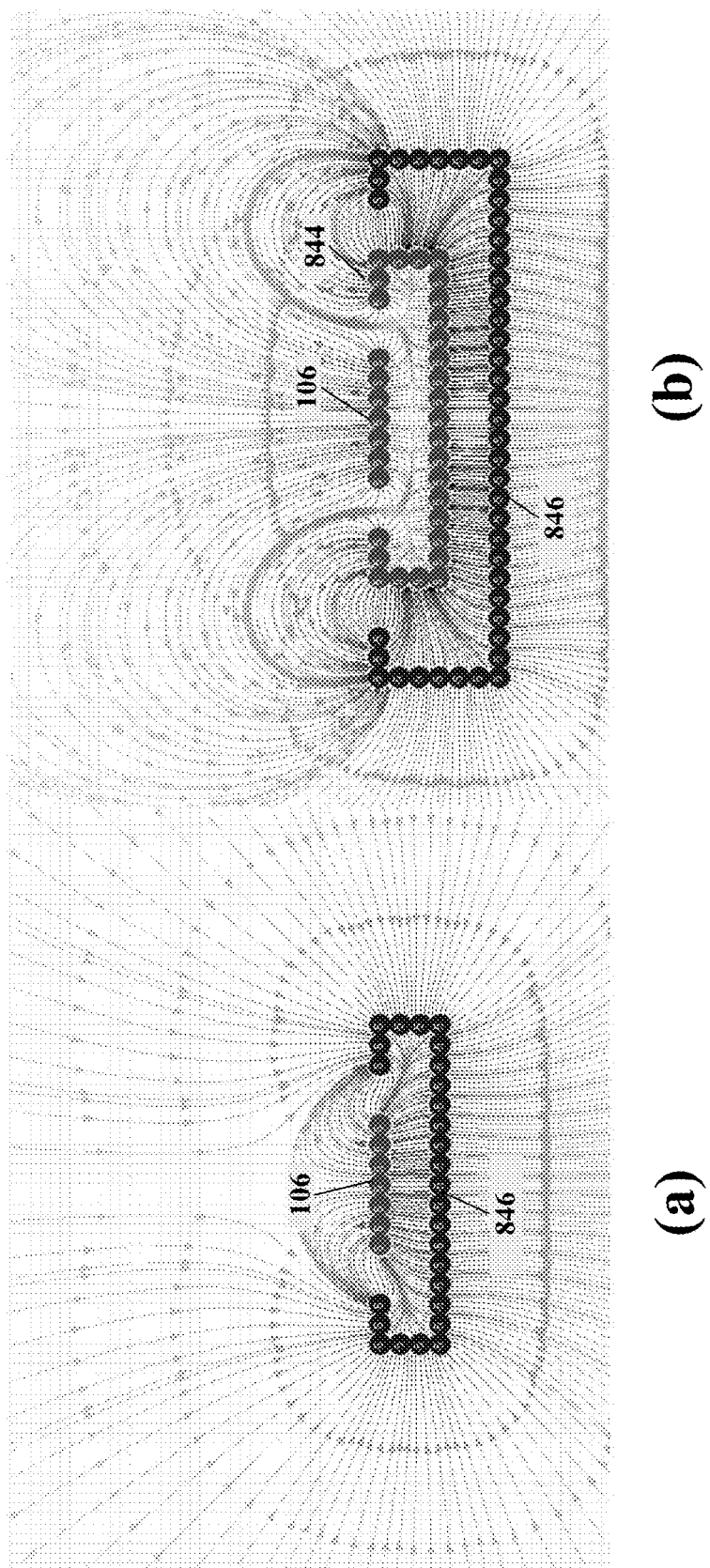
FIG. 14 illustrates schematic representations of electrostatic field lines surrounding a capacitive plate in close proximity to a grounded conductive plane, and electrostatic field lines surrounding a capacitive plate with a guard ring between the capacitive plate and grounded conductive plan.

Referring to FIG. 14, depicted are schematic representations of electrostatic field lines surrounding a capacitive plate in close proximity to a grounded conductive plane, FIG. 14(a), and electrostatic field lines surrounding a capacitive plate with a guard ring between the capacitive plate and grounded conductive plane, FIG. 14(b). A schematic representation of electrostatic fields between the electrode 106 and surrounding conductors at different voltage potentials are shown in FIG. 14(a). Note the strong electrostatic field lines between the electrode 106 and surrounding metal and/or conductors, e.g., ground plane 846. This parasitic capacitance limits detection resolution of a change in the capacitance value of the electrode 106 occurring during smoke entry into the chamber 102. Parasitic capacitance similarly affects the connections between the electrode 106 and the microcontroller 1024 or 1124. It also limits the amount of noise shielding that may be employed in ion chamber smoke detectors.

A guard ring 844 may be introduced around the electrode 106 of the ion chamber 102. By maintaining a voltage on the guard ring 844 that is substantially the same as the voltage on the electrode 106, parasitic capacitances may be significantly reduced. Thereby increasing detection resolution of a change in the leaky capacitance value of the ion chamber 102 occurring during smoke entry therein. In addition, the guard ring 844 may enhance noise shielding of the electrode 106 and ion chamber 102.

FIG. 14(b) shows a schematic representation of electrostatic fields between the electrode 106, guard ring 844 and a ground plane 846, if present, wherein the electrode 106 and the guard ring 844 are at substantially the same voltage potential. Note the much weaker electrostatic field lines (longer lines) between the electrode 106 and the ground plane 846. There is substantially no parasitic capacitance between the electrode 106 and the guard ring 844 because both are at substantially the same voltage potential. Referring back to FIGS. 10 and 11, an analog driver 842 may be coupled to an analog bus 846 which is also coupled to the GPIO connection 538b and the capacitor 220. The guard ring 844 may be coupled to the GPIO connection 840 which may also coupled to an analog driver 842. The analog driver 842 may drive the guard ring 844 to the charge voltage on the capacitor 220 which may be at substantially the same voltage as on the electrode 106, thereby reducing the electrostatic fields between the electrode 106 and surrounding grounded metal.

Figure 15:
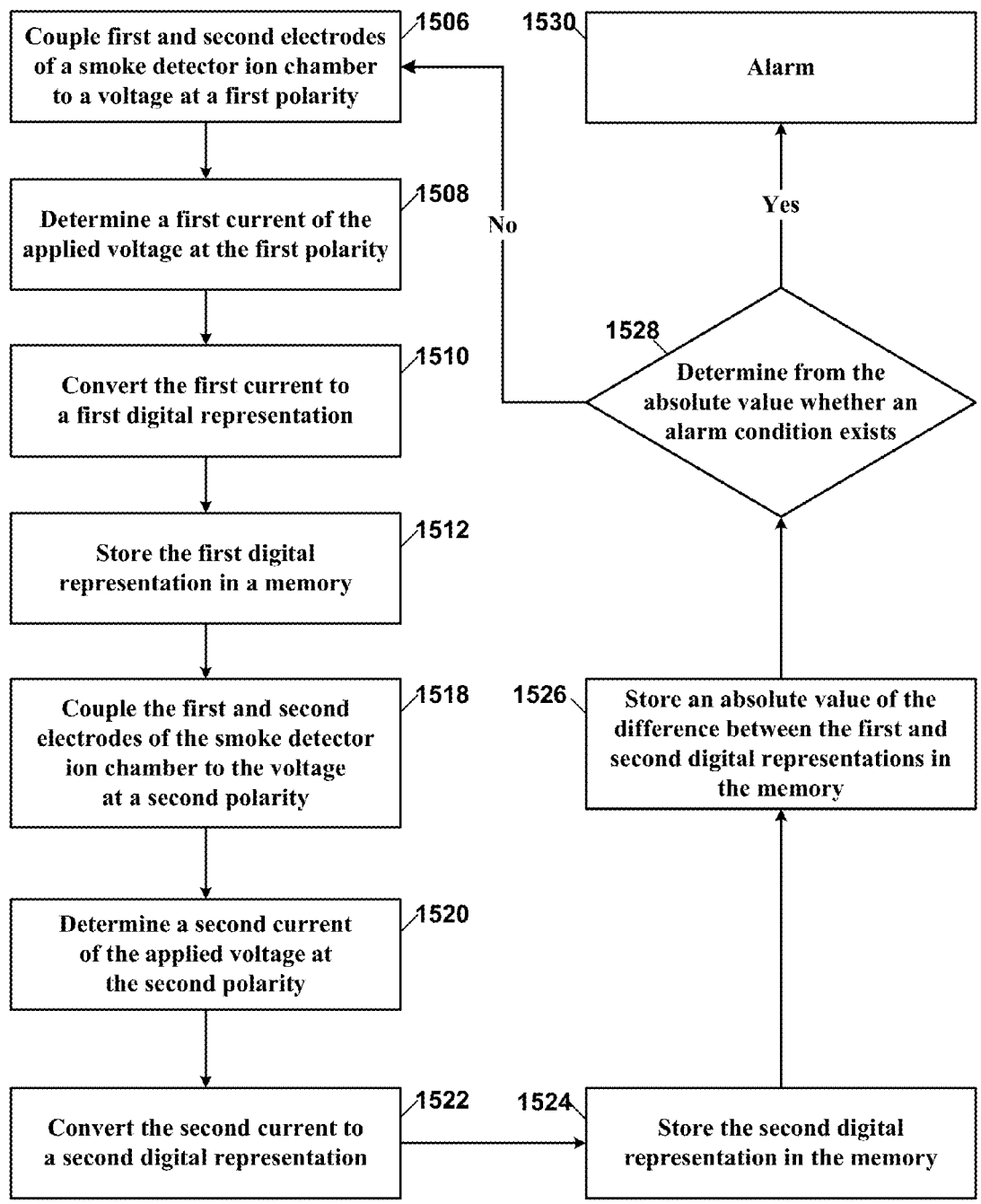
FIGS. 15, 16, 17 and 18 illustrate operational schematic process flow diagrams, according to the teachings and embodiments of this disclosure.

Referring to FIG. 15, depicted is a schematic operational process flow diagram, according to the teachings and embodiments of this disclosure. In step 1506 first and second electrodes of a smoke detector ion chamber 102 are coupled to a voltage at a first polarity. In step 1508 a first current resulting from application to the ion chamber 102 of the first polarity voltage is determined. In step 1510 the first current is converted to a first digital representation thereof. In step 1512 the first digital representation is stored in a memory for further processing. In step 1518 the first and second electrodes of the smoke detector ion chamber 102 are coupled to the voltage at a second polarity. In step 1520 a second current resulting from application of the second polarity voltage is determined. In step 1522 the second current is converted to a second digital representation thereof. In step 1524 the second digital representation is stored in the memory for further processing.

In step 1526 an absolute value, i.e., positive value, of the difference between the first and the second digital representations is stored in the memory. This difference value is representative of the ion current 116 through the ion chamber 102 with the common mode leakage current 114 removed therefrom. In step 1528 a determination is made from the difference value whether a smoke detection alarm condition exists. This determination may be made by comparing the difference value to a reference value, comparing a prior difference value to a present difference value, and/or the rate of change of a plurality of difference values. When an alarm condition exists, an alarm may be generated in step 1530.

Figure 16:
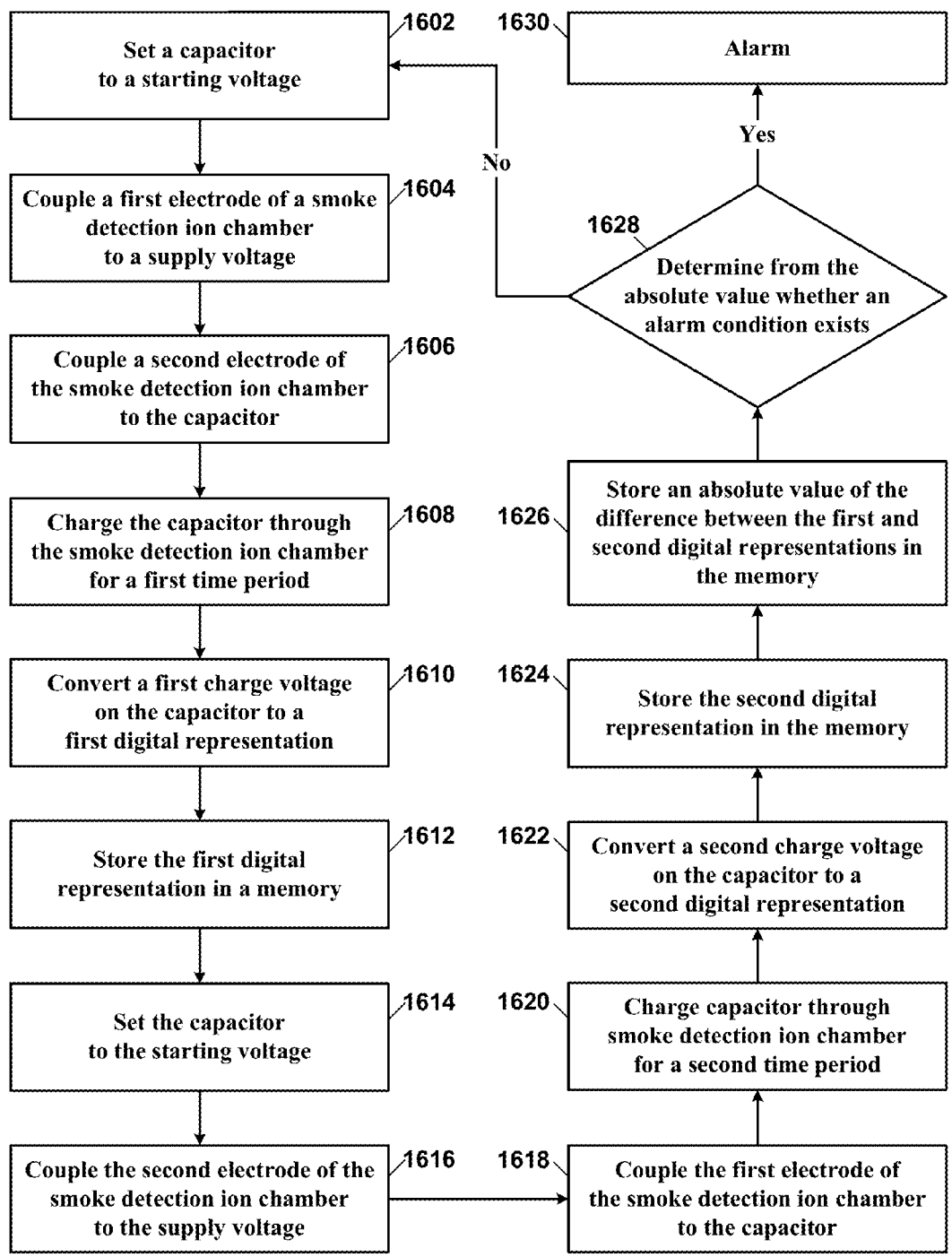

Referring to FIG. 16, depicted is a schematic operational process flow diagram, according to the teachings and embodiments of this disclosure. In step 1602 a capacitor 220 is set to a starting voltage, e.g., zero (0) volts, e.g., $V_{SS}$, or coupled to a supply voltage, e.g., $V_{DD}$. In step 1604 a first electrode 104 of a smoke detection ion chamber 102 is connected to a supply voltage 112. In step 1606 a second electrode 106 of the smoke detection ion chamber 102 is connected to the capacitor 220. In step 1608 the capacitor 220 is charged with the ion current 116 through the ion chamber 102 and the leakage current 114 during a first time period. In step 1610 a resulting charge voltage on the capacitor 220 is converted to a first digital representation thereof. In step 1612 the first digital representation is stored in a memory for further processing.

In step 1614 the capacitor 220 is set to the starting voltage. In step 1616 the second electrode 106 of a smoke detection ion chamber 102 is connected to the supply voltage 112. In step 1618 the first electrode 104 of the smoke detection ion chamber 102 is connected to the capacitor 220. In step 1620 the capacitor 220 is charged with only the leakage current 114 during a second time period. In step 1622 a resulting charge voltage on the capacitor 220 is converted to a second digital representation thereof. In step 1624 the second digital representation is stored in a memory for further processing.

In step 1626 an absolute value, i.e., positive value, of the difference between the first and the second digital representations is stored in the memory. This difference value is representative of the ion current 116 through the ion chamber 102 with the common mode leakage current 114 removed therefrom. In step 1628 a determination is made from the difference value whether a smoke detection alarm condition exists. This determination may be made by comparing the difference value to a reference value, comparing a prior difference value to a present difference value, and/or the rate of change of a plurality of difference values. When an alarm condition exists, an alarm may be generated in step 1630.

Figure 17:
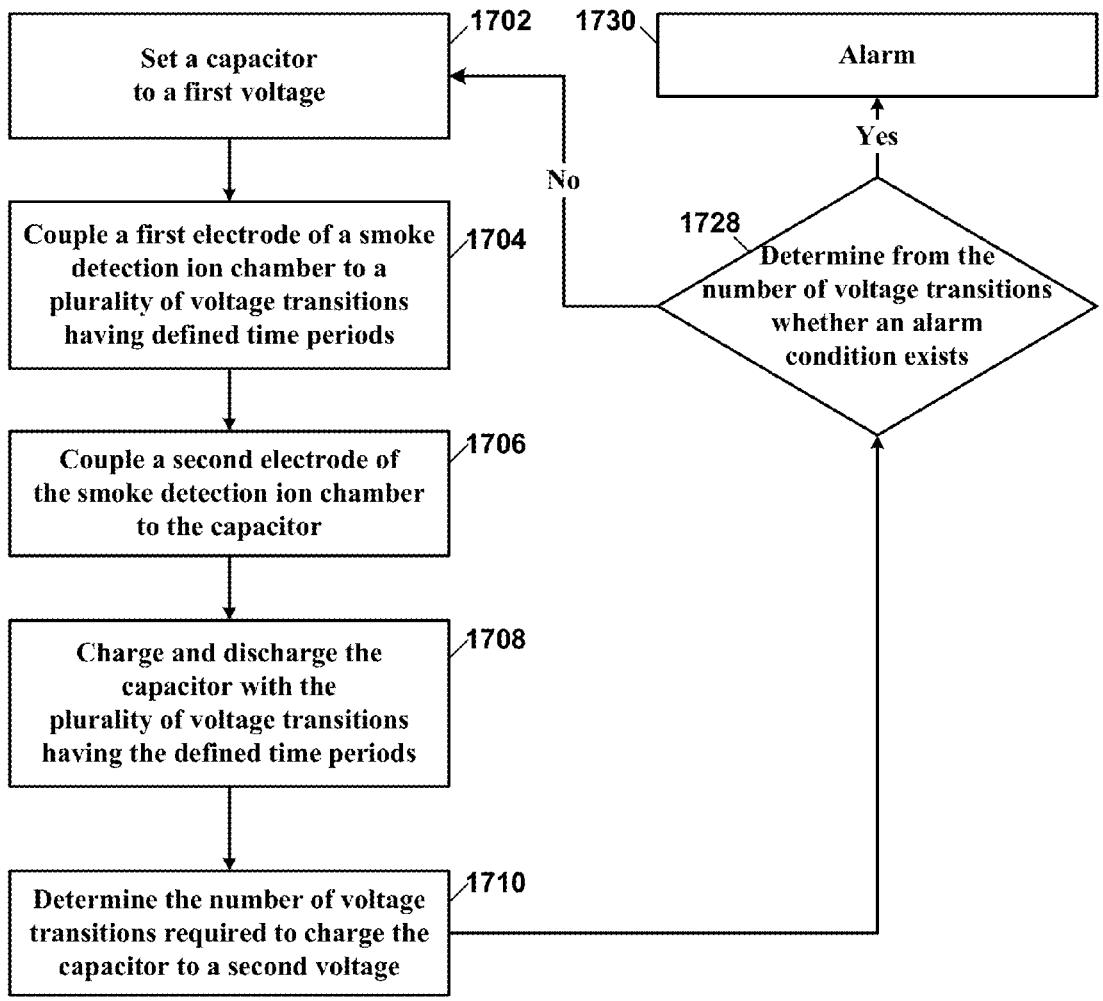

Referring to FIG. 17, depicted is a schematic operational process flow diagram, according to the teachings and embodiments of this disclosure. In step 1702 a capacitor 220 is set to a first voltage. In step 1704 a first electrode 104 of a smoke detection ion chamber 102 is connected to a plurality of voltage transitions having defined time periods from a pulse generator 1050. In step 1706 a second electrode 106 of the smoke detection ion chamber 102 is connected to the capacitor 220. In step 1708 the plurality of voltage transitions from substantially zero volts during a first time period to a supply voltage during a second time period are applied to the first electrode 104 of the smoke detection ion chamber 102. Wherein the capacitor 220 is charged at an ion current 116 through the ion chamber 102 plus a leakage current 114 when the voltage transitions are at the supply voltage, and the capacitor 220 is discharged at the leakage current 114 when the voltage transitions are at substantially zero volts. Step 1710 determines a number of voltage transitions required to charge the capacitor to a second voltage. In step 1728 a determination is made from the number of voltage transitions whether a smoke detection alarm condition exists. Wherein when the alarm condition exists, an alarm may be generated in step 1730. The number of voltage transitions may be used in determining an alarm condition, and/or the number of voltage transitions within a certain time period thereof.

The first and second time periods may be substantially equal or adjusted according to a value of a charge voltage on the capacitor 220, wherein when the charge voltage is less than half of the supply voltage the first time period may be greater than the second time period, and when the charge voltage is great than half of the supply voltage the first time period may be less than the second time period. This feature may be used to more linearly charge and discharge the capacitor 220 as the charge voltage thereon goes from less than to greater than one half of the supply voltage. When the charge voltage on the capacitor 220 is about one-half of the supply voltage, the first and second time periods may be substantially the same. A pulse width modulation (PWM) generator 1050 may be used to generate these variable duty cycle pulses to charge and discharge the capacitor 220.

Figure 18:
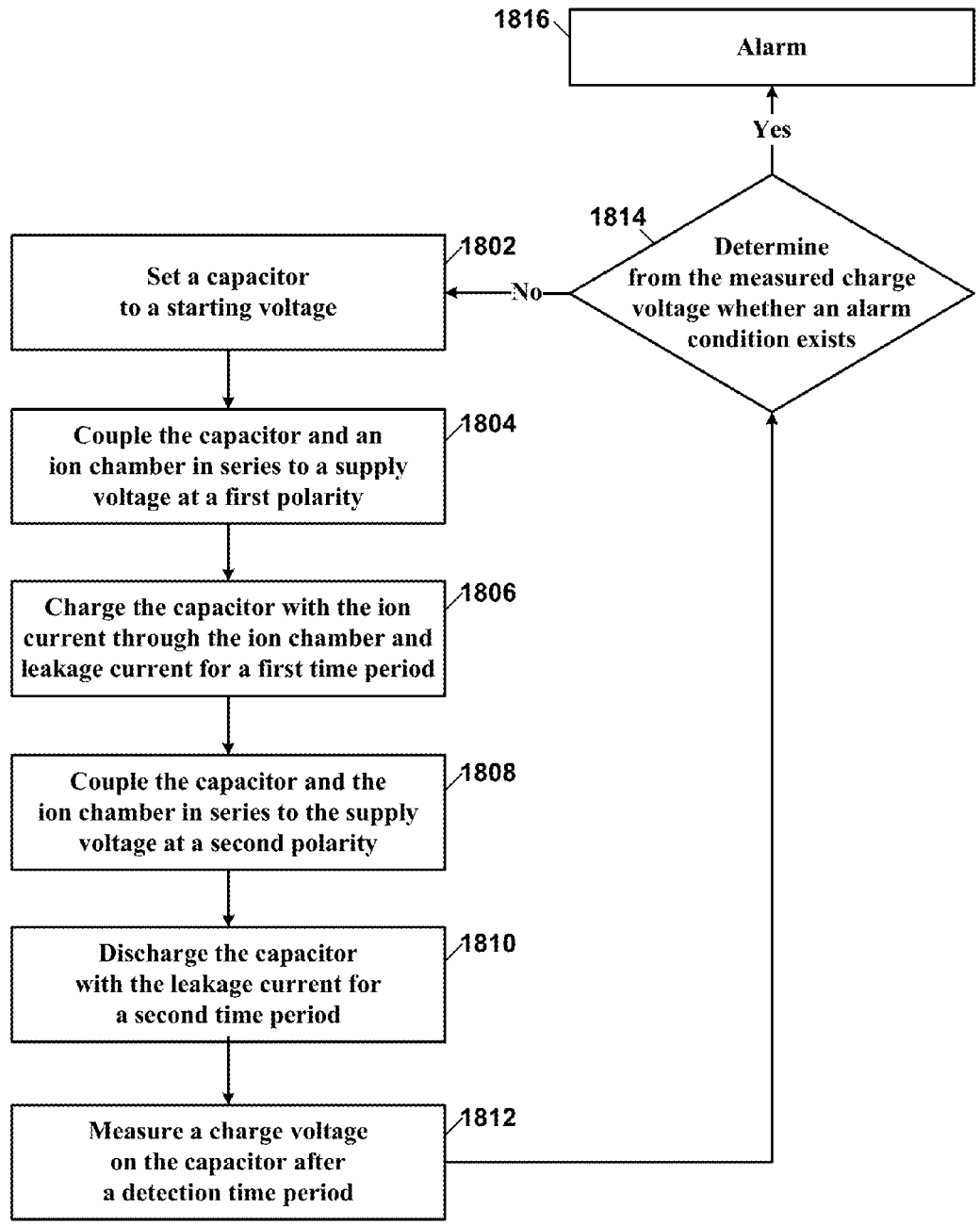

Referring to FIG. 18, depicted is a schematic operational process flow diagram, according to the teachings and embodiments of this disclosure. In step 1802 a capacitor 220 is set to a starting voltage, e.g., zero (0) volts, e.g., $V_{SS}$, or coupled to a supply voltage, e.g., $V_{DD}$. In step 1804 a smoke detection ion chamber 102 and the capacitor 220 are coupled in series to a supply voltage at a first polarity. In step 1806 the capacitor 220 is charged with ionization current through the ion chamber 102 and leakage current for a first time period.

In step 1808 the smoke detection ion chamber 102 and the capacitor 220 are coupled in series to the supply voltage at a second polarity, wherein the second polarity may be the opposite of the first polarity. In step 1810 the capacitor 220 is discharged with the leakage current for a second time period. In step 1812 a charge voltage on the capacitor 220 is measured after a detection time period.

In step 1814 a determination is made from the measured charge voltage whether a smoke detection alarm condition exists. This determination may be made by comparing the measured voltage to a reference value, comparing a prior measured voltage to a present measured voltage, and/or the rate of change of a plurality of difference measured voltages over time. When an alarm condition exists, an alarm may be generated in step 1816.

It is contemplated and within the scope of this disclosure that the capacitor 220 may first be fully charged to a voltage instead of being discharged to substantially zero (0) volts, then the ion chamber is coupled to the capacitor 220 in such a way that the ion electron current 116 and the leakage current 114 will discharge the capacitor 220 and only the leakage current 114 will charge the capacitor 220. Since the combination of the ion electron current 116 and the leakage current 114 is greater than just the leakage current 114 alone, the capacitor will eventually discharge to about zero (0) volts.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A method for determining ion current in an ion chamber, said method comprising the steps of:
   coupling first and second electrodes of an ion chamber to a voltage at a first polarity;
   determining a first current between the first and the second electrodes of the ion chamber caused by the voltage at the first polarity;
   coupling the first and the second electrodes of the ion chamber to the voltage at a second polarity;
   determining a second current between the first and the second electrodes of the ion chamber caused by the voltage at the second polarity; and
   determining a difference between the first and second currents, wherein the difference is the ion current through the ion chamber.

2. The method according to claim 1, wherein the second polarity is opposite the first polarity.

3. The method according to claim 1, wherein the voltage is a direct current (DC) voltage.

4. The method according to claim 1, wherein the ion chamber comprises a radiation source for ionizing gas molecules therein.

5. The method according to claim 1, wherein the ion chamber is used to detect smoke particles.

6. The method according to claim 1, wherein the step of determining the difference between the first and second currents comprises the steps of:
    storing the first and second current measurements in a memory; and
    subtracting one current measurement from the other current measurement.

7. The method according to claim 1, wherein the voltage is a plurality of voltage pulses.

8. The method according to claim 1, wherein
    the step of coupling the first and second electrodes to a voltage at a first polarity comprises:
        setting a capacitor to a starting voltage;
        coupling the first electrode of the ion chamber to a supply voltage;
        coupling the second electrode of the ion chamber to the capacitor; and
        charging the capacitor for a first period of time;
    the step of determining a first current comprises:
        converting a first charge voltage on the capacitor to a first digital representation thereof; and
        storing the first digital representation in a memory;
    the step of of coupling the first and second electrodes to the voltage at a second polarity comprises:
        setting the capacitor to the starting voltage;
        coupling the second electrode of the ion chamber to the supply voltage;
        coupling the first electrode of the ion chamber to the capacitor; and
        charging the capacitor for a second period of time;
    and wherein the step of determining a second current comprises:
        converting a second charge voltage on the capacitor to a second digital representation thereof; and
        storing the second digital representation in the memory.

9. The method according to claim 8, wherein the starting voltage is substantially zero (0) volts.

10. The method according to claim 8, wherein the starting voltage is substantially the supply voltage.

11. The method according to claim 8, further comprising the step of determining whether the difference is in an alarm condition range.

12. The method according to claim 11, further comprising the step of actuating an alarm when the difference is in the alarm condition range.

13. The method according to claim 8, wherein the voltage is a pulse generator comprising a plurality of output voltage pulses.

14. The method according to claim 8, further comprising the step of charging a guard ring around the ion chamber to a voltage on the capacitor.

15. The method according to claim 1, wherein
    the step of coupling the first and second electrodes to a voltage at a first polarity comprises:
        setting a capacitor to a starting voltage;
        coupling the first electrode of an ion chamber to a pulse source;
        coupling the second electrode of the ion chamber to the capacitor; and
        charging the capacitor with a plurality of pulses from the pulse source for a first period of time;
    the step of determining a first current comprises:
        counting a first number of the plurality of pulses required to charge the capacitor to a second voltage; and
        storing the first number in a memory;
    the step of coupling the first and second electrodes to the voltage at a second polarity comprises:
        setting the capacitor to the supply voltage;
        coupling the second electrode of the ion chamber to the pulse source;
        coupling the first electrode of the ion chamber to the capacitor;
        charging the capacitor with the plurality of pulses from the pulse source for a second period of time;
    the step of determining a second current comprises:
        counting a second number of the plurality of pulses required to charge the capacitor to the second voltage; and
        storing the second number in a memory.

16. The method according to claim 15, wherein the starting voltage is substantially zero (0) volts.

17. The method according to claim 15, wherein the starting voltage is substantially the supply voltage.

18. The method according to claim 15, further comprising the step of determining whether the difference is in an alarm condition range.

19. The method according to claim 18, further comprising the step of actuating an alarm when the difference is in the alarm condition range.

20. The method according to claim 15, further comprising the step of charging a guard ring around the ion chamber to a voltage on the capacitor.

21. The method according to claim 15, wherein
    to the plurality of pulses are formed by a plurality of voltage transitions having time periods and voltage amplitudes from substantially zero volts to substantially a voltage.

22. The method according to claim 21, further comprising the step of determining whether the number of transitions represents an alarm condition range.

23. The method according to claim 21, further comprising the steps of:
    measuring a charge voltage on the capacitor; and
    adjusting the time periods for the plurality of voltage transitions when at substantially zero volts and at substantially the voltage, wherein:
        when the charge voltage on the capacitor is less than one-half the voltage, the time periods of the plurality of voltage transitions when at the zero volt amplitude are greater than the time periods of the plurality of voltage transitions when at the voltage amplitude;
        when the charge voltage on the capacitor is at substantially one-half the voltage, the time periods of the zero volt and voltage amplitudes of the plurality of voltage transitions are substantially the same; and
        when the charge voltage on the capacitor is greater than one-half the voltage, the time periods of the plurality of voltage transitions when at the zero volt amplitude are less than the time periods of the plurality of voltage transitions when at the voltage amplitude.

24. The method according to claim 21, further comprising the step of charging a guard ring around the ion chamber to substantially the charge voltage on the capacitor.

25. A method for determining ion current in an ion chamber, said method comprising the steps of:
    setting a capacitor to a starting voltage;
    coupling an ion chamber and a capacitor in series to a supply voltage at a first polarity;
    charging the capacitor for a first time period;
    coupling the ion chamber and the capacitor in series to the supply voltage at a second polarity;
    discharging the capacitor for a second time period; and measuring a charge voltage on the capacitor after a detection time period.

26. The method according to claim 25, wherein the starting voltage is substantially zero (0) volts.

27. The method according to claim 25, wherein the starting voltage is substantially the supply voltage.

28. The method according to claim 25, further comprising the step of determining whether the measured charge voltage is in an alarm condition range.

29. The method according to claim 28, further comprising the step of actuating an alarm when the measured charge voltage is in the alarm condition range.

30. The method according to claim 25, wherein the supply voltage is a pulse generator having an output comprising a plurality of voltage pulses.

31. The method according to claim 25, further comprising the step of charging a guard ring around the ion chamber to substantially the charge voltage on the capacitor.

* * * * *